(12) United States Patent
Sun

(10) Patent No.: US 10,980,792 B2
(45) Date of Patent: Apr. 20, 2021

(54) FORMULATIONS OF CABOZANTINIB

(71) Applicants: Zhuhai Beihai Biotech Co., Ltd., Zhuhai (CN); Qun Sun, Princeton, NJ (US)

(72) Inventor: Qun Sun, Princeton, NJ (US)

(73) Assignee: Zhuhai Beihai Biotech Co., Ltd.

( * ) Notice: Subject to any disclaimer, the term of this patent is extended or adjusted under 35 U.S.C. 154(b) by 0 days.

(21) Appl. No.: 16/332,159

(22) PCT Filed: Sep. 11, 2017

(86) PCT No.: PCT/US2017/050965
§ 371 (c)(1),
(2) Date: Mar. 11, 2019

(87) PCT Pub. No.: WO2018/049329
PCT Pub. Date: Mar. 15, 2018

(65) Prior Publication Data
US 2019/0358217 A1   Nov. 28, 2019

Related U.S. Application Data

(60) Provisional application No. 62/393,506, filed on Sep. 12, 2016.

(51) Int. Cl.
*A61K 9/00* (2006.01)
*A61P 35/00* (2006.01)
*A61K 31/47* (2006.01)
*A61K 47/64* (2017.01)

(52) U.S. Cl.
CPC ............ *A61K 31/47* (2013.01); *A61K 47/643* (2017.08)

(58) Field of Classification Search
None
See application file for complete search history.

(56) References Cited

U.S. PATENT DOCUMENTS

| 8,877,776 B2 | 11/2014 | Brown | |
|---|---|---|---|
| 2012/0022065 A1* | 1/2012 | Bannen | A61P 9/00 514/235.2 |
| 2014/0363514 A1 | 12/2014 | Koyakutty et al. | |
| 2015/0342945 A1 | 12/2015 | Xi | |
| 2016/0022662 A1 | 1/2016 | DeCillis | |
| 2016/0095942 A1 | 4/2016 | Markovic et al. | |

FOREIGN PATENT DOCUMENTS

WO   WO 2015/177758   11/2015

OTHER PUBLICATIONS

Kratz, "Albumin as a drug carrier: Design of prodrugs, drug conjugates and nanoparticles," J. Controlled release 132:171-183 (2008) (Year: 2008).*
Sigma, "Product Information: Albumin, Human" Oct. 9, 1996, 2 pages.
Cayman Chemical, "Product Information XL 184" Apr. 25, 2015, 1 page.
International Search Report and Written Opinion for App. Ser. No. PCT/US2017/050965, dated Nov. 24, 2017, 8 pages.
Bentzien et al., "In Vitro and In Vivo Activity of Cabozantinib (XL184), an Inhibitor of RET, MET, and VEGFR2, in a Model of Medullary Thyroid Cancer", Thyroid, 23: 1569-1577, 2013.
Bosse et al., "Phase I Comparability of Recombinant Human Albumin and Human Serum Albumin", J Clin. Pharmacol., 45: 57-67, 2005.
Carter et al., "Structure of Serum Albumin", Adv. Protein. Chem., 45, 153-203, 1994.
Chen et al., "Human serum albumin from recombinant DNA technology: Challenges and strategies", Biochimica et Biophysica Acta., 1830: 5515-5525, 2013.
Chen, "Removal of Fatty Acids from Serum Albumin by Charcoal Treatment", J Biol. Chem., 242: 173-181, 1967.
Cohn et al., "Preparation and Properties of Serum and Plasma Proteins. IV. A System for the Separation into Fractions of the Protein and Lipoprotein Components of Biological Tissues and Fluids", J Am. Chem. Soc., 68: 459-475, 1946.
Curry et al., "Crystal structure of human serum albumin complexed with fatty acid reveals an asymmetric distribution of binding sites", Nat. Struct. Biol., 5, 827-35, 1998.
Fehske et al., "The location of drug binding sites in human serum albumin", Biochem. Pharmcol., 30, 687-92, 1981.
Finlayson, "Albumin Products", Seminars in Thrombosis and Hemostasis, 6, 85-120, 1980.
Goodman et al., The Pharmacological Basis of Therapeutics, 9th ed, JVIcGraw-Hill New York, 1996.
Hauser et al., "Oxygen transport responses to colloids and crystalloids in critically ill surgical patients.", Surgery, Gynecology and Obstetrics, 150, 811-816, 1980.
He et al., "Atomic structure and chemistry of human serum albumin", Nature, 358, 209-15, 1992.
Kragh Hansen, "Structure and ligand binding properties of human serum albumin", Dan. Aled Bull., 1441, 131-40, 1990.
Lee et al., "An intravenous formulation decision tree for discovery compound formulation development", International Journal of Pharmaceutics 253, 111-119, 2003.
Lin et al., "Stability of Human Serum Albumin During Bioprocessing: Denaturation and Aggregation During Processing of Albumin Paste", Pharmaceutical Research, 17:391-6, 2000.

(Continued)

*Primary Examiner* — Julie Ha
*Assistant Examiner* — Kristina M Hellman
(74) *Attorney, Agent, or Firm* — Fish & Richardson P.C.

(57) ABSTRACT

This document relates to compositions comprising a non-covalently bound complex comprising cabozantinib and human serum albumin, wherein the cabozantinib and the human serum albumin in the composition have a ratio by weight from about 1:5 to about 1:2000. This document also relates to compositions comprising cabozantinib and human serum albumin, wherein the cabozantinib and the human serum albumin in the composition have a ratio by weight from about 1:5 to about 1:2000. This document also relates to compositions consisting essentially of cabozantinib and human serum albumin, wherein the cabozantinib and the human serum albumin in the composition have a ratio by weight from about 1:5 to about 1:2000.

16 Claims, No Drawings

(56) References Cited

OTHER PUBLICATIONS

Sugio et al., "Crystal structure of human serum albumin at 2.5 Å resolution", Protein. Eng., 12, 439-46, 1999.
Tullis, "Albumin", JAAIA, 237, 355-360, 460-463, 1977.
Vorum, "Reversible ligand binding to human serum albumin. Theoretical and clinical aspects.", Dan. Med. Bull., 46, 379-99, 1999.
Yakes et al., "Cabozantinib (XL184), a Novel MET and VEGFR2 Inhibitor, Simultaneously Suppresses Metastasis, Angiogenesis, and Tumor Growth", Mol Cancer Ther, 10: 2298-2308, 2011.
Yang et al., "Cabozantinib Loaded DSPE-PEG2000 Micelles as Delivery System: Formulation, Characterization and Cytotoxicity Evaluation", BAOJ Pharm Sci., 1: 1-20, 2015.

* cited by examiner

FORMULATIONS OF CABOZANTINIB

CLAIM OF PRIORITY

This application is the National Stage of international application No. PCT/US2017/050965, filed Sep. 11, 2017, which claims the benefit of U.S. provisional application No. 62/393,506 filed Sep. 12, 2016. The entire contents of the foregoing are hereby incorporated by reference.

TECHNICAL FIELD

This document relates to compositions and formulations for the treatment of proliferative diseases, and more particularly to compositions and formulations comprising cabozantinib.

BACKGROUND

Cabozantinib is a small molecule inhibitor of multiple receptor tyrosine kinases, including MET (hepatocyte growth factor receptor), VEGFR2 (vascular endothelial growth factor receptor2), also known as KDR (kinase insert domain containing receptor), and RET (rearranged during transfection), which are implicated in tumor growth, angiogenesis, and metastatic progression of cancer (Yakes et al., *Mol Cancer Ther* 2011; 10:2298-2308; Bentzien et al., *Thyroid* 2013; 23: 1569-1577).

Cabozantinib (marketed under the name COMETRIQ) has been approved in the United States and European Union for the treatment of subjects with progressive metastatic medullary thyroid cancer. In addition, more recently, cabozantinib (marketed under the name CABOMETYX) is approved by the US Food and Drug administration (FDA) and indicated for the treatment of patients with advanced renal cell carcinoma (RCC) who have received prior anti-angiogenic therapy.

Cabozantinib is hydrophobic and practically insoluble in water. Therefore, it has been administered mainly via the oral route in a tablet or capsule formulation to patients. Its very poor water solubility prevents its administration by the intravenous route (IV), which may be important in patients unable to take cabozantinib orally. A PEG-lipid-based polymeric micelle formulation for IV delivery of cabozantinib has been developed (Yang et al., *BAOJ Pharm Sci.* 2015; 1: 1-20). However, there is a need in the art for suitable IV formulations of cabozantinib which are less toxic and with no synthetic polymer used in the IV formulations. The compositions and methods described in the present application help meet this need.

SUMMARY

Provided herein is a composition comprising a non-covalently bound complex comprising cabozantinib and human serum albumin, wherein the cabozantinib and the human serum albumin in the composition have a ratio by weight from about 1:5 to about 1:2000.

In some embodiments, the cabozantinib and the human serum albumin in the composition have a ratio by weight from about 1:100 to about 1:2000, from about 1:130 to about 1:1000, from about 1:130 to about 1:500, from about 1:140 to about 1:500, from about 1:150 to about 1:800, from about 1:150 to about 1:700, from about 1:150 to about 1:600, from about 1:150 to about 1:500, from about 1:150 to about 1:400, from about 1:150 to about 1:350, from about 1:150 to about 1:300, from about 1:160 to about 1:700, from about 1:160 to about 1:600, from about 1:160 to about 1:500, from about 1:160 to about 1:400, from about 1:160 to about 1:350, from about 1:160 to about 1:300, from about 1:165 to about 1:700, from about 1:165 to about 1:600, from about 1:165 to about 1:500, from about 1:165 to about 1:400, from about 1:165 to about 1:350, from about 1:165 to about 1:300, from about 1:170 to about 1:700, from about 1:170 to about 1:600, from about 1:170 to about 1:500, from about 1:170 to about 1:400, from about 1:170 to about 1:350, from about 1:170 to about 1:300, from about 1:150 to about 1:250, from about 1:160 to about 1:250, from about 1:165 to about 1:250, or from about 1:170 to about 1:250. In some embodiments, the cabozantinib and the human serum albumin have a ratio by weight of about 1:130, about 1:140, about 1:150, about 1:155, about 1:160, about 1:162.5, about 165, about 1:170, about 1:175, about 1:180, about 1:190, about 1:200, about 1:210, about 1:220, about 1:230, about 1:240, about 1:250, about 1:260, about 1:270, or about 1:280, about 1:290, about 1:300, about 1:350, about 1:400, or about 1:500.

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free.

Also, provided herein is a composition comprising cabozantinib and human serum albumin, wherein the cabozantinib and the human serum albumin in the composition have a ratio by weight from about 1:5 to about 1:2000.

In some embodiments, the cabozantinib and the human serum albumin in the composition have a ratio by weight from about 1:100 to about 1:2000, from about 1:130 to about 1:1000, from about 1:130 to about 1:500, from about 1:140 to about 1:500, from about 1:150 to about 1:800, from about 1:150 to about 1:700, from about 1:150 to about 1:600, from about 1:150 to about 1:500, from about 1:150 to about 1:400, from about 1:150 to about 1:350, from about 1:150 to about 1:300, from about 1:160 to about 1:700, from about 1:160 to about 1:600, from about 1:160 to about 1:500, from about 1:160 to about 1:400, from about 1:160 to about 1:350, from about 1:160 to about 1:300, from about 1:165 to about 1:700, from about 1:165 to about 1:600, from about 1:165 to about 1:500, from about 1:165 to about 1:400, from about 1:165 to about 1:350, from about 1:165 to about 1:300, from about 1:170 to about 1:700, from about 1:170 to about 1:600, from about 1:170 to about 1:500, from about 1:170 to about 1:400, from about 1:170 to about 1:350, from about 1:170 to about 1:300, from about 1:150 to about 1:250, from about 1:160 to about 1:250, from about 1:165 to about 1:250, or from about 1:170 to about 1:250. In some embodiments, the cabozantinib and the human serum albumin have a ratio by weight of about 1:130, about 1:140, about 1:150, about 1:155, about 1:160, about 1:162.5, about 165, about 1:170, about 1:175, about 1:180, about 1:190, about 1:200, about 1:210, about 1:220, about 1:230, about 1:240, about 1:250, about 1:260, about 1:270, or about 1:280, about 1:290, about 1:300, about 1:350, about 1:400, or about 1:500.

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free.

In some embodiments, the composition is a clear aqueous solution when the composition is dissolved in an aqueous solution. In some embodiments, the aqueous solution is substantially free of solvent other than water. In some embodiments, the aqueous solution is free of solvent other than water.

In some embodiments, the composition is a clear aqueous solution for at least about 1 hour, 2 hours, 3 hours, 4 hours, 5 hours, 6 hours, 8 hours, or 24 hours, when the composition is dissolved in an aqueous solution.

In some embodiments, the composition is a solid formulation. For example, the solid formulation can be produced in a uniform manner by lyophilization. A skilled artisan would recognize other methods, such as rotary evaporation, that can also produce solid formulations.

In some embodiments, the composition is an aqueous formulation. In some embodiments, the aqueous formulation is substantially free of solvent other than water. In some embodiments, the aqueous formulation is free of solvent other than water.

In some embodiments, the aqueous formulation is a clear aqueous solution. For example, the formulation can be a clear and stable aqueous solution reconstituted from a sterile lyophilized powder. In some embodiments, the aqueous formulation is a clear aqueous solution, wherein the aqueous formulation is substantially free of solvent other than water. In some embodiments, the solution remains clear for at least about 2 hours, 4 hours, 6 hours, 8 hours, 10 hours, 12 hours, 20 hours, 24 hours, 2 days, 3 days, 4 days, 5 days, 6 days or a week.

Also, provided herein is a pharmaceutical composition comprising the composition comprising the cabozantinib and the human serum albumin as described herein, and a pharmaceutically acceptable carrier.

In some embodiments, the pharmaceutical composition is free of a surfactant, such as CREMOPHOR® surfactants and Polysorbate 80. In some embodiments, the pharmaceutical composition is substantially free of a surfactant, such as CREMOPHOR® surfactants and Polysorbate 80. In some embodiments, the pharmaceutical composition can be substantially free of a surfactant selected from the group consisting of CREMOPHOR® surfactants and Polysorbate 80.

Also, provided herein is a method of treating a cancer, the method comprising the step of administering to a subject in need thereof of a therapeutically effective amount of a pharmaceutical composition comprising the composition comprising the cabozantinib and the human serum albumin as described herein, and a pharmaceutically acceptable carrier.

In some embodiments, the cancer is a solid tumor. In some embodiments, the cancer is selected from the group consisting of thyroid cancer, renal cell carcinoma (RCC), kidney cancer, hepatocellular cancer, non-small cell lung cancer, ovarian cancer, glioblastoma, melanoma, and colorectal cancer. In some embodiments, the cancer is a thyroid cancer. In some embodiments, the cancer is a metastatic medullary thyroid cancer. In some embodiments, the cancer is a renal cell carcinoma (RCC). In some embodiments, the cancer is an advanced renal cell carcinoma (RCC) who have received prior antiangiogenic therapy. In some embodiments the cancer is a kidney cancer. In some embodiments, the cancer is a hepatocellular cancer.

Also, provided herein is a composition consisting essentially of cabozantinib and human serum albumin, wherein the cabozantinib and the human serum albumin in the composition have a ratio by weight from about 1:5 to about 1:2000.

In some embodiments, the cabozantinib and the human serum albumin in the composition have a ratio by weight from about 1:100 to about 1:2000, from about 1:130 to about 1:1000, from about 1:130 to about 1:500, from about 1:140 to about 1:500, from about 1:150 to about 1:800, from about 1:150 to about 1:700, from about 1:150 to about 1:600, from about 1:150 to about 1:500, from about 1:150 to about 1:400, from about 1:150 to about 1:350, from about 1:150 to about 1:300, from about 1:160 to about 1:700, from about 1:160 to about 1:600, from about 1:160 to about 1:500, from about 1:160 to about 1:400, from about 1:160 to about 1:350, from about 1:160 to about 1:300, from about 1:165 to about 1:700, from about 1:165 to about 1:600, from about 1:165 to about 1:500, from about 1:165 to about 1:400, from about 1:165 to about 1:350, from about 1:165 to about 1:300, from about 1:170 to about 1:700, from about 1:170 to about 1:600, from about 1:170 to about 1:500, from about 1:170 to about 1:400, from about 1:170 to about 1:350, from about 1:170 to about 1:300, from about 1:150 to about 1:250, from about 1:160 to about 1:250, from about 1:165 to about 1:250, or from about 1:170 to about 1:250. In some embodiments, the cabozantinib and the human serum albumin have a ratio by weight of about 1:130, about 1:140, about 1:150, about 1:155, about 1:160, about 1:162.5, about 165, about 1:170, about 1:175, about 1:180, about 1:190, about 1:200, about 1:210, about 1:220, about 1:230, about 1:240, about 1:250, about 1:260, about 1:270, or about 1:280, about 1:290, about 1:300, about 1:350, about 1:400, or about 1:500.

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free.

In some embodiments, the composition is a clear aqueous solution when the composition is dissolved in an aqueous solution. In some embodiments, the aqueous solution is substantially free of solvent other than water. In some embodiments, the aqueous solution is free of solvent other than water.

In some embodiments, the composition is a clear aqueous solution for at least about 1 hour, 2 hours, 3 hours, 4 hours, 5 hours, 6 hours, 8 hours, or 24 hours, when the composition is dissolved in an aqueous solution.

In some embodiments, the composition is a solid formulation. For example, the solid formulation can be produced in a uniform manner by lyophilization. A skilled artisan would recognize other methods, such as rotary evaporation, that can also produce solid formulations.

In some embodiments, the composition is an aqueous formulation. In some embodiments, the aqueous formulation is substantially free of solvent other than water. In some embodiments, the aqueous formulation is free of solvent other than water.

In some embodiments, the aqueous formulation is a clear aqueous solution. For example, the formulation can be a clear and stable aqueous solution reconstituted from a sterile lyophilized powder. In some embodiments, the aqueous formulation is a clear aqueous solution, wherein the aqueous formulation is substantially free of solvent other than water. In some embodiments, the solution remains clear for at least about 2 hours, 4 hours, 6 hours, 8 hours, 10 hours, 12 hours, 20 hours, 24 hours, 2 days, 3 days, 4 days, 5 days, 6 days or a week.

Also, provided herein is a pharmaceutical composition comprising the composition consisting essentially of the cabozantinib and the human serum albumin as described herein, and a pharmaceutically acceptable carrier.

Also, provided herein is a method of treating a cancer, the method comprising the step of administering to a subject in need thereof of a therapeutically effective amount of a pharmaceutical composition comprising the composition consisting essentially of the cabozantinib and the human serum albumin as described herein, and a pharmaceutically acceptable carrier.

In some embodiments, the cancer is a solid tumor. In some embodiments, the cancer is selected from the group consisting of thyroid cancer, renal cell carcinoma (RCC), kidney cancer, hepatocellular cancer, non-small cell lung cancer, ovarian cancer, glioblastoma, melanoma, and colorectal cancer. In some embodiments, the cancer is a thyroid cancer. In some embodiments, the cancer is a metastatic medullary thyroid cancer. In some embodiments, the cancer is a renal cell carcinoma (RCC). In some embodiments, the cancer is an advanced renal cell carcinoma (RCC) who have received prior antiangiogenic therapy. In some embodiments the cancer is a kidney cancer. In some embodiments, the cancer is a hepatocellular cancer.

Also provided herein is a composition comprising cabozantinib and human serum albumin, wherein the ratio by weight of cabozantinib and the human serum albumin in the composition is from about 1:5 to about 1:2000, produced by a method comprising the steps of:

(i) obtaining an organic solution of cabozantinib in a polar water-miscible organic solvent;

(ii) obtaining a first aqueous solution of human serum albumin; and (iii) mixing the organic solution of cabozantinib and the first aqueous solution of human serum albumin to obtain a second aqueous solution comprising the composition comprising cabozantinib and human serum albumin.

In some embodiments, the present disclosure provides a composition consisting essentially of cabozantinib and human serum albumin, wherein the cabozantinib and the human serum albumin in the composition have a ratio by weight from about 1:5 to about 1:2000, produced by a method comprising the steps of:

(i) obtaining an organic solution of cabozantinib in a polar water-miscible organic solvent;

(ii) obtaining a first aqueous solution of human serum albumin; and (iii) mixing the organic solution of cabozantinib and the first aqueous solution of human serum albumin to obtain a second aqueous solution comprising the composition comprising cabozantinib and human serum albumin.

In some embodiments, the human serum albumin is essentially fatty acid free.

In some embodiments, the composition comprises a non-covalently bound complex comprising the cabozantinib and the human serum albumin.

In some embodiments, the amount of aqueous solvent in the first aqueous solution is from about 0.01 mL to about 0.05 mL per 1 mg of human serum albumin.

In some embodiments, the polar water-miscible organic solvent is an alcohol selected from the group consisting of methanol, ethanol, isopropanol, n-butanol, and mixtures thereof.

In some embodiments, the polar water-miscible organic solvent is selected from methanol, ethanol, and mixtures thereof.

In some embodiments, the aqueous solvent is water.

In some embodiments, the mixing comprises adding the organic solution to the first aqueous solution.

In some embodiments, wherein the mixing comprises adding the first aqueous solution to the organic solution.

In some embodiments, the mixing is carried out at a temperature from about 0° C. to about 25° C.

In some embodiments, the mixing is carried out at a temperature from about 0° C. to about 5° C.

In some embodiments, the mixing is carried out at about 0° C.

In some embodiments, the composition is prepared by further comprising the step of removing the polar water-miscible organic solvent from the second aqueous solution to obtain a third aqueous solution comprising the composition comprising cabozantinib and human serum albumin. In some embodiments, the composition is prepared by further comprising the step of removing aqueous solvent from the third aqueous solution to obtain the composition comprising cabozantinib and human serum albumin.

In some embodiments, the composition is prepared by further comprising the step of removing the organic solvent and the aqueous solvent from the second aqueous solution to obtain the composition comprising cabozantinib and human serum albumin.

In some embodiments, the removing as carried out in vacuum.

In some embodiments, the removing is carried out by lyophilization.

In some embodiments, the composition forms a clear aqueous solution when the composition is dissolved in an aqueous solvent, and wherein the solubility of the composition in the aqueous solution is at least 10 mg/ml.

In some embodiments, the composition is a solid formulation

In some embodiments, the composition is an aqueous formulation.

In some embodiments, the aqueous formulation is substantially free of solvent other than water.

In some embodiments, the aqueous formulation is free of a surfactant.

In some embodiments, the surfactant is selected from the group consisting of CREMOPHOR® surfactants and Polysorbate 80.

In some embodiments, the aqueous formulation is a clear aqueous solution.

In some embodiments, the aqueous formulation is a clear aqueous solution for at least 1 hour, at least 2 hours, at least 3 hours, at least 4 hours, at least 5 hours, at least 6 hours, at least 8 hours, or at least 24 hours.

In some embodiments, the present disclosure provides a pharmaceutical composition comprising the composition as prepared by a process as described herein, and a pharmaceutically acceptable carrier.

In some embodiments, the present disclosure provides a method of treating a cancer, the method comprising the step of administering to a subject in need thereof a therapeutically effective amount of the pharmaceutical composition as described herein.

In some embodiments, the cancer is a solid tumor. In some embodiments, the cancer is selected from the group consisting of thyroid cancer, renal cell carcinoma (RCC), kidney cancer, hepatocellular cancer, non-small cell lung cancer, ovarian cancer, glioblastoma, melanoma, and colorectal cancer. In some embodiments, the cancer is a thyroid cancer. In some embodiments, the cancer is a metastatic medullary thyroid cancer. In some embodiments, the cancer is a renal cell carcinoma (RCC). In some embodiments, the cancer is an advanced renal cell carcinoma (RCC) who have received prior antiangiogenic therapy. In some embodiments the cancer is a kidney cancer. In some embodiments, the cancer is a hepatocellular cancer.

DETAILED DESCRIPTION

Provided herein is a composition comprising a non-covalently bound complex comprising cabozantinib and human serum albumin, wherein the cabozantinib and the human serum albumin in the composition have a ratio by weight from about 1:5 to about 1:2000.

In some embodiments, the cabozantinib and the human serum albumin in the composition have a ratio by weight from about 1:100 to about 1:2000, from about 1:130 to about 1:1000, from about 1:130 to about 1:500, from about 1:140 to about 1:500, from about 1:150 to about 1:800, from about 1:150 to about 1:700, from about 1:150 to about 1:600, from about 1:150 to about 1:500, from about 1:150 to about 1:400, from about 1:150 to about 1:350, from about 1:150 to about 1:300, from about 1:160 to about 1:700, from about 1:160 to about 1:600, from about 1:160 to about 1:500, from about 1:160 to about 1:400, from about 1:160 to about 1:350, from about 1:160 to about 1:300, from about 1:165 to about 1:700, from about 1:165 to about 1:600, from about 1:165 to about 1:500, from about 1:165 to about 1:400, from about 1:165 to about 1:350, from about 1:165 to about 1:300, from about 1:170 to about 1:700, from about 1:170 to about 1:600, from about 1:170 to about 1:500, from about 1:170 to about 1:400, from about 1:170 to about 1:350, from about 1:170 to about 1:300, from about 1:150 to about 1:250, from about 1:160 to about 1:250, from about 1:165 to about 1:250, or from about 1:170 to about 1:250. In some embodiments, the cabozantinib and the human serum albumin have a ratio by weight of about 1:130, about 1:140, about 1:150, about 1:155, about 1:160, about 1:162.5, about 165, about 1:170, about 1:175, about 1:180, about 1:190, about 1:200, about 1:210, about 1:220, about 1:230, about 1:240, about 1:250, about 1:260, about 1:270, or about 1:280, about 1:290, about 1:300, about 1:350, about 1:400, or about 1:500.

In some embodiments, the non-covalent interaction between cabozantinib and human serum albumin in the complex comprises hydrogen bonding. In some embodiments, the non-covalent interaction between cabozantinib and human serum albumin in the complex comprises electrostatic interaction. In some embodiments, the non-covalent interaction between cabozantinib and human serum albumin in the complex comprises hydrophobic interaction. In some embodiments, the non-covalent interaction between cabozantinib and human serum albumin in the complex comprises Van der Waals forces. In some embodiments, the non-covalent interaction between cabozantinib and human serum albumin in the complex comprises hydrogen bonding, electrostatic interaction, hydrophobic interactions and Van der Waals forces.

In some embodiments, the non-covalent interaction between cabozantinib and human serum albumin in the composition comprises hydrogen bonding. In some embodiments, the non-covalent interaction between cabozantinib and human serum albumin in the composition comprises electrostatic interaction. In some embodiments, the non-covalent interaction between cabozantinib and human serum albumin in the composition comprises hydrophobic interaction. In some embodiments, the non-covalent interaction between cabozantinib and human serum albumin in the composition comprises Van der Waals forces. In some embodiments, the non-covalent interaction between cabozantinib and human serum albumin in the composition comprises hydrogen bonding, electrostatic interaction, hydrophobic interactions and Van der Waals forces.

As used herein, the term "human serum albumin" refers to native and recombinant human serum albumin. Native human serum albumin and other plasma proteins can be precipitated from human plasma by varying the pH and adding ethanol, in what is known as the Cohn fractionation process (Cohn E J et al., *J. Am. Chem. Soc.* 1946; 68:459-475). By controlling the pH and ethanol content, semi-purified fractions of plasma proteins can be produced. One of the last proteins to precipitate in the Cohn process is native human serum albumin. After precipitation, a wet paste of crude native human serum albumin is obtained. Subsequent bioprocessing steps (purification, filtration, pasteurization, etc.) can be used to produce a purified, stabilized form of native human serum albumin for commercial use (Lin J J et al., *Pharmaceutical Research* 2000; 17:391-6). Recombinant human serum albumin is a highly purified animal-, virus-, and prion-free product as alternative to native human serum albumin, to which it is structurally equivalent (Bosse D et al., *J Clin. Pharmacol.* 2005; 45:57-67). Recombinant human serum albumin has been produced by various hosts, both prokaryotic and eukaryotic (Chen Z et al., *Biochimica et Biophysica Acta* 2013; 1830:5515-5525). A fatty acid free human serum albumin can be prepared by treatment of human serum albumin with charcoal at low pH. Likewise, treatment of human serum albumin with charcoal at low pH can be used to remove fatty acids from human serum albumin (Chen R F, *J. Biol. Chem.* 1967; 242:173-181).

Human serum albumin (HSA) is a highly soluble globular protein of Mr 65K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Intravenous use of HSA solution has been indicated for the prevention and treatment of hypovolumic shock (see, e.g., Tullis, *JAMA,* 237, 355-360, 460-463, (1977) and Houser et al., *Surgery, Gynecology and Obstetrics,* 150, 811-816 (1980)) and in conjunction with exchange transfusion in the treatment of neonatal hyperbilirubinemia (see, e.g., Finlayson, *Seminars in Thrombosis and Hemostasis,* 6, 85-120, (1980)).

Human serum albumin (HSA) has multiple hydrophobic binding sites (a total of seven for medium and long-chain fatty acids, an endogenous ligand of HSA) and binds a diverse set of drugs, especially neutral and negatively charged hydrophobic compounds (Goodman et al., *The Pharmacological Basis of Therapeutics,* 9th ed, McGraw-Hill New York (1996)). Two high affinity binding sites have been proposed in subdomains IIA and IIIA of HSA, which are highly elongated hydrophobic pockets with charged lysine and arginine residues near the surface which function as attachment points for polar ligand features (see, e.g., Fehske et al., *Biochem. Pharmcol.,* 30, 687-92 (1981), Vorum, Dan. Med. Bull., 46, 379-99 (1999), Kragh-Hansen, Dan. *Med Bull.,* 1441, 131-40 (1990), Curry et al., *Nat. Struct. Biol.,* 5, 827-35 (1998), Sugio et al., *Protein. Eng.,* 12, 439-46 (1999), He et al., *Nature,* 358, 209-15 (1992), and Carter et al., *Adv. Protein. Chem.,* 45, 153-203 (1994)).

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free. In some embodiments, the human serum albumin contains no more than two moles of fatty acids bound to one mole of human serum albumin. In some embodiments, the human serum albumin contains no more than one mole of fatty acids bound to one mole of human serum albumin. In some embodiments, human serum albumin contains no more than 0.5 moles of fatty acids bound to one mole of human serum albumin. In some embodiments, the human serum albumin contains no more than 0.1 moles of fatty acids bound to one mole of human serum albumin. In some embodiments, the human serum albumin contains no more than 0.05 moles of fatty acids bound to one mole of human serum albumin. In some embodiments, the human serum albumin contains no more than 0.01 moles of fatty acids bound to one mole of human serum albumin. In some embodiments, the human serum albumin contains no more than 0.001 moles of fatty acids bound to one mole of human serum albumin. In some embodiments, the human serum albumin contains no more than 0.0005 moles of fatty acids bound to one mole of human serum albumin. In some embodiments, the human serum albumin contains no more than 0.0001 moles of fatty acids bound to one mole of human serum albumin.

As used herein, the term "non-covalently bound complex" refers to a complex in which the bonds between the components of the complex are non-covalent bonds (e.g., weak bonds such as hydrogen bonds, electrostatic effects, π-effects, hydrophobic effects and Van der Waals forces). Further, human serum albumin (HSA) has multiple hydrophobic binding sites (a total of seven for medium and long-chain fatty acids, an endogenous ligand of HSA) and binds a diverse set of drugs, especially neutral and negatively charged hydrophobic compounds (Goodman et al., The Pharmacological Basis of Therapeutics, 9th ed, McGraw-Hill New York (1996)). Additionally, after the drug molecule binds to HSA, the drug molecule and HSA form a non-covalently bound drug and protein complex through the binding sites of HSA. This concept is commonly understood by one of ordinary skill in the art to which this disclosure belongs. One example of a non-covalently bound complex is a non-covalently bound complex of HSA and fatty acids, in which the fatty acids bind to HSA through HSA's multiple binding sites.

As used herein, the term "stable" refers to non-covalently bound complexes that do not readily disassociate and aggregate into their separate parts, e.g., do not readily dissociate and aggregate for a period of time of greater than 6 hours, 12 hours, 24 hours, or 3 days). For example, a solution including stable non-covalently bound complexes will often appear transparent whereas a solution including unstable non-covalently bound complexes will appear translucent or cloudy. Further, it will be appreciated by those of ordinary skill in the art, that after a period of time, stable non-covalently bound complexes can disassociate and aggregate into their separate parts. Thus, a solution including stable non-covalently bound complexes can become translucent or cloudy after a period of time (e.g., 6 hours, 12 hours, 24 hours, or 3 days).

The oral volume of distribution ($V_z/F$) of cabozantinib is approximately 319 L. Cabozantinib is highly protein bound in human plasma (≥99.7%). See CABOMETYX Prescribing Information.

As used herein, the term "essentially fatty acid free" refers to proteins (e.g. serum albumin) that contain less than about 0.02% fatty acid by weight. For example, human serum albumin that is essentially fatty acid free can contain less than 0.02% fatty acid by weight.

As used herein, the term "fatty acids" refers to non-esterified fatty acids (e.g. linoleic acid, α-linoleic acid, γ-linoleic acid).

As used herein the term cabozantinib is a compound that has the CAS No. 849217-88-1 and the following chemical structure:

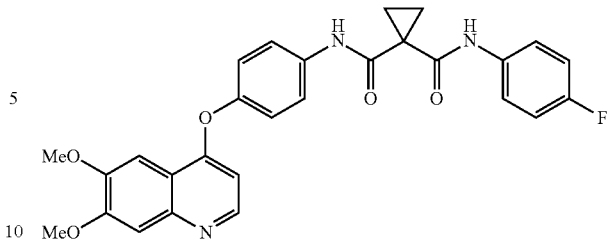

Cabozantinib is a white to off-white solid and is practically insoluble in water.

Further, cabozantinib is a kinase inhibitor indicated for the treatment of patients with progressive metastatic medullary thyroid cancer and for the treatment of patients with advanced renal cell carcinoma (RCC) who have received prior antiangiogenic therapy.

Cabozantinib is also in phase 1 clinical trial in combination with gemcitabine for the treatment of advanced pancreatic cancer, phase 2 clinical trial for the treatment of non-small cell lung cancer (NSCLC), phase 2 clinical trial in combination with erlotinib hydrochloride for the treatment of recurrent non-small cell lung carcinoma and stage IV non-small cell lung cancer, phase 1 clinical trial in combination with vemurafenib for the treatment of recurrent melanoma, stage IIIA melanoma, stage IIIB melanoma, stage IIIC melanoma and stage IV melanoma, phase 1 clinical trial in combination with pilimumab (with or without pilimumab) for the treatment of malignant reproductive system neoplasm, malignant urinary system neoplasm, metastatic urethral neoplasm, metastatic urothelial carcinoma of the renal pelvis and ureter, progressive neoplastic disease, recurrent bladder carcinoma, recurrent urethra carcinoma, recurrent urothelial carcinoma of the renal pelvis and ureter, regional urothelial carcinoma of the renal pelvis and ureter, solid neoplasm, stage III bladder urothelial carcinoma, stage III urethral cancer, stage IV bladder urothelial carcinoma, stage IV urethral cancer and urethral urothelial carcinoma, phase 2 clinical trial for the treatment of lung cancer and solid tumor (not breast or prostate cancers), phase 2 clinical trial for the treatment of Merkel cell carcinoma and skin cancer, phase 2 clinical trial for the treatment of adrenal cortex carcinoma, adult alveolar soft part sarcoma, adult clear cell sarcoma of soft parts, adult hepatocellular carcinoma, adult rhabdomyosarcoma, adult soft tissue sarcoma, childhood alveolar soft part sarcoma, childhood central nervous system neoplasm, childhood clear cell sarcoma of soft parts, childhood hepatocellular carcinoma, childhood rhabdomyosarcoma, childhood soft tissue sarcoma, childhood solid neoplasm, Ewing sarcoma, hepatoblastoma, hepatocellular carcinoma, recurrent adrenal cortex carcinoma, recurrent adult hepatocellular carcinoma, recurrent adult soft tissue sarcoma, recurrent alveolar soft part sarcoma, recurrent childhood central nervous system neoplasm, recurrent childhood hepatocellular carcinoma, recurrent childhood soft tissue sarcoma, recurrent Ewing sarcoma, recurrent hepatoblastoma, recurrent renal cell carcinoma, recurrent rhabdomyosarcoma, relapsed solid neoplasm, renal cell carcinoma, thyroid gland medullary carcinoma, and Wilms tumor, phase 2 clinical trial in combination with androgen ablation therapy for the treatment of prostate cancer, phase 2 clinical trial for the treatment of poorly differentiated thyroid gland carcinoma, recurrent thyroid gland carcinoma, stage I thyroid gland follicular carcinoma, stage I thyroid gland papillary carcinoma, stage II thyroid gland follicular carcinoma, stage II thyroid gland papillary carcinoma, stage III thyroid gland follicular carcinoma, stage III thyroid gland papillary carcinoma, stage IVA thyroid gland follicular carcinoma, stage IVA thyroid gland papillary carcinoma, stage IVB thyroid gland follicular carcinoma, stage IVB thyroid gland papillary carcinoma, stage IVC thyroid gland follicular carcinoma, stage IVC thyroid gland papillary carcinoma, tall cell variant thyroid gland papillary carcinoma and thyroid gland oncocytic follicular carcinoma, and other clinical trials, all of which are incorporated herein by reference.

In some embodiments, the cabozantinib can be a pharmaceutically acceptable salt of cabozantinib.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively. In some embodiments, pharmaceutically acceptable salts may be preferred over the respective free base or free acid because such salts impart greater stability or solubility to the molecule thereby facilitating formulation into a dosage form. Basic compounds are generally capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate (e.g., S-malate), tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), napthalene-2-sulfonate, ethanedisulfonate, hydrogen bisulfide, bitartrate, gluconate, glucuronate, para-bromophenylsulfonate, carbonate, pyrosulfate, sulfite, bisulfate, monohydrogen phosphate, dihydrogen phosphate, metaphosphate, pyrophosphate, chloride, bromide, iodide, decanoate, caprylate, caprate, propiolate, suberate, sebacate, butyne-1,4-dioate, hexyne-1,6-dioate, terephthalate, sulfonate, xylenesulfonate, phenylpropionate, phenylbutyrate, β-hydroxybutyrate, glycolate, propanesulfonate, naphthalene-1-sulfonate, naphthalene-2-sulfonate and 2,5-dihydroxybenzoate. Suitable bases include pharmaceutically acceptable inorganic bases and pharmaceutically acceptable organic bases. Representative pharmaceutically acceptable base addition salts include hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, cabozantinib is a malate salt of cabozantinib. In some embodiments, cabozantinib is a (S)-malate salt of cabozantinib.

In some embodiments, cabozantinib is crystalline. In some embodiments, the (S)-malate salt of cabozantinib is crystalline. In some embodiments, the (S)-malate salt of cabozantinib is any one of the crystalline forms disclosed, for example, in U.S. Pat. No. 8,877,776 and PCT publication No. WO2015177758, the disclosures of each of the above are incorporated herein by reference in their entirety.

In some embodiments, cabozantinib is in amorphous. In some embodiments. cabozantinib is any one of the amorphous forms disclosed.

In some embodiments, the composition is a clear aqueous solution when the composition is dissolved in an aqueous solution. In some embodiments, the aqueous solution is substantially free of solvent other than water. In some embodiments, the aqueous solution is free of solvent other than water.

In some embodiments, the composition forms a clear aqueous solution, when the composition is dissolved in an aqueous solution, wherein the clear aqueous solution has pH value from about 5 to about 8. In some embodiments, the composition forms a clear aqueous solution, when the composition is dissolved in an aqueous solution, wherein the clear aqueous solution has pH value from about 5.5 to about 7.8. In some embodiments, the composition forms a clear aqueous solution, when the composition is dissolved in an aqueous solution, wherein the clear aqueous solution has pH value from about 6 to about 7.5. In some embodiments, the composition forms a clear aqueous solution, when the composition is dissolved in an aqueous solution, wherein the clear aqueous solution has pH value from about 6.5 to about 7.5. In some embodiments, the composition forms a clear aqueous solution, when the composition is dissolved in an aqueous solution, wherein the clear aqueous solution has pH value from about 6 to about 6.5. In some embodiments, the composition forms a clear aqueous solution, when the composition is dissolved in an aqueous solution, wherein the clear aqueous solution has pH value from about 6.5 to about 7. In some embodiments, the composition forms a clear aqueous solution, when the composition is dissolved in an aqueous solution, wherein the clear aqueous solution has pH value from about 7 to about 7.5. In some embodiments, the composition forms a clear aqueous solution, when the composition is dissolved in an aqueous solution, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous formulation is substantially free of solvent other than water. In some embodiments, the aqueous formulation is free of solvent other than water.

In some embodiments, the composition is a clear aqueous solution for at least about 1 hour, 2 hours, 3 hours, 4 hours, 5 hours, 6 hours, 8 hours, or 24 hours, when the composition is dissolved in an aqueous solution. In some embodiments, the aqueous solution is substantially free of solvent other than water. In some embodiments, the aqueous solution is free of solvent other than water.

In some embodiments, the composition is a solid formulation. For example, the solid formulation can be produced in a uniform manner by lyophilization. A skilled artisan would recognize other methods, such as rotary evaporation, that can also produce solid formulations.

In some embodiments, the composition is an aqueous formulation. In some embodiments, the aqueous formulation is substantially free of solvent other than water. In some embodiments, the aqueous formulation is free of solvent other than water.

In some embodiments, the aqueous formulation is a clear aqueous solution. For example, the formulation can be a clear and stable aqueous solution reconstituted from a sterile lyophilized powder. In some embodiments, the aqueous formulation is a clear aqueous solution, wherein the aqueous formulation is substantially free of solvent other than water. In some embodiments, the aqueous formulation is a clear aqueous solution, wherein the aqueous formulation is free of solvent other than water.

In some embodiments, the aqueous formulation is a clear aqueous solution reconstituted from the solid formulation (e.g. the sterile lyophilized powder) in water. In some embodiments, the aqueous formulation is a clear aqueous solution reconstituted from the solid formulation (e.g. the sterile lyophilized powder) in 0.9% saline solution. In some embodiments, the aqueous formulation is a clear aqueous solution reconstituted from the solid formulation (e.g. the sterile lyophilized powder) in 5% Dextrose water solution.

In some embodiments, the aqueous formulation has pH value from about 5 to about 8. In some embodiments, the aqueous formulation has pH value from about 5.5 to about 7.8. In some embodiments, the aqueous formulation has pH value from about 6 to about 7.5. In some embodiments, the aqueous formulation has pH value from about 6.5 to about 7.5. In some embodiments, the aqueous formulation has pH value from about 6 to about 6.5. In some embodiments, the aqueous formulation has pH value from about 6.5 to about 7. In some embodiments, the aqueous formulation has pH value from about 7 to about 7.5. In some embodiments, the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous formulation is substantially free of solvent other than water. In some embodiments, the aqueous formulation is free of solvent other than water.

In some embodiments, the aqueous formulation is a clear aqueous solution for at least 1 hour. In some embodiments, the aqueous formulation is a clear aqueous solution for at least 2 hours. In some embodiments, the aqueous formulation is a clear aqueous solution for at least 3 hours. In some embodiments, the aqueous formulation is a clear aqueous solution for at least 4 hours. In some embodiments, the aqueous formulation is a clear aqueous solution for at least 5 hours. In some embodiments, the aqueous formulation is a clear aqueous solution for at least 6 hours. In some embodiments, the aqueous formulation is a clear aqueous solution for at least 8 hours. In some embodiments, the aqueous formulation is a clear aqueous solution for at least 24 hours. In some embodiments, the solution remains clear for at least about 2 hours, 4 hours, 6 hours, 8 hours, 10 hours, 12 hours, 20 hours, 24 hours, 2 days, 3 days, 4 days, 5 days, 6 days or a week.

Also, provided herein is a pharmaceutical composition comprising the composition comprising the cabozantinib and the human serum albumin as described herein, and a pharmaceutically acceptable carrier.

In some embodiments, the pharmaceutical composition is free of a surfactant, such as CREMOPHOR® surfactants and Polysorbate 80. In some embodiments, the pharmaceutical composition is substantially free of a surfactant, such as CREMOPHOR® surfactants and Polysorbate 80. In some embodiments, the pharmaceutical composition can be substantially free of a surfactant selected from the group consisting of CREMOPHOR® surfactants and Polysorbate 80.

Also, provided herein is a method of treating a cancer, the method comprising the step of administering to a subject in need thereof of a therapeutically effective amount of a pharmaceutical composition comprising the composition comprising the cabozantinib and the human serum albumin as described herein, and a pharmaceutically acceptable carrier.

In some embodiments, the cancer is a solid tumor. In some embodiments, the cancer is selected from the group consisting of thyroid cancer, renal cell carcinoma (RCC), kidney cancer, hepatocellular cancer, non-small cell lung cancer, ovarian cancer, glioblastoma, melanoma, and colorectal cancer. In some embodiments, the cancer is a thyroid cancer. In some embodiments, the cancer is a metastatic medullary thyroid cancer. In some embodiments, the cancer is a renal cell carcinoma (RCC). In some embodiments, the cancer is an advanced renal cell carcinoma (RCC) who have received prior antiangiogenic therapy. In some embodiments the cancer is a kidney cancer. In some embodiments, the cancer is a hepatocellular cancer.

Also, provided herein is a composition comprising cabozantinib and human serum albumin, wherein the cabozantinib and the human serum albumin in the composition have a ratio by weight from about 1:5 to about 1:2000.

In some embodiments, the cabozantinib and the human serum albumin in the composition have a ratio by weight from about 1:100 to about 1:2000, from about 1:130 to about 1:1000, from about 1:130 to about 1:500, from about 1:140 to about 1:500, from about 1:150 to about 1:800, from about 1:150 to about 1:700, from about 1:150 to about 1:600, from about 1:150 to about 1:500, from about 1:150 to about 1:400, from about 1:150 to about 1:350, from about 1:150 to about 1:300, from about 1:160 to about 1:700, from about 1:160 to about 1:600, from about 1:160 to about 1:500, from about 1:160 to about 1:400, from about 1:160 to about 1:350, from about 1:160 to about 1:300, from about 1:165 to about 1:700, from about 1:165 to about 1:600, from about 1:165 to about 1:500, from about 1:165 to about 1:400, from about 1:165 to about 1:350, from about 1:165 to about 1:300, from about 1:170 to about 1:700, from about 1:170 to about 1:600, from about 1:170 to about 1:500, from about 1:170 to about 1:400, from about 1:170 to about 1:350, from about 1:170 to about 1:300, from about 1:150 to about 1:250, from about 1:160 to about 1:250, from about 1:165 to about 1:250, or from about 1:170 to about 1:250. In some embodiments, the cabozantinib and the human serum albumin have a ratio by weight of about 1:130, about 1:140, about 1:150, about 1:155, about 1:160, about 1:162.5, about 165, about 1:170, about 1:175, about 1:180, about 1:190, about 1:200, about 1:210, about 1:220, about 1:230, about 1:240, about 1:250, about 1:260, about 1:270, or about 1:280, about 1:290, about 1:300, about 1:350, about 1:400, or about 1:500.

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free. In some embodiments, the human serum albumin contains no more than two moles of fatty acids bound to one mole of human serum albumin. In some embodiments, the human serum albumin contains no more than one mole of fatty acids bound to one mole of human serum albumin. In some embodiments, human serum albumin contains no more than 0.5 moles of fatty acids bound to one mole of human serum albumin. In some embodiments, the human serum albumin contains no more than 0.1 moles of fatty acids bound to one mole of human serum albumin. In some embodiments, the human serum albumin contains no more than 0.05 moles of fatty acids bound to one mole of human serum albumin. In some embodiments, the human serum albumin contains no more than 0.01 moles of fatty acids bound to one mole of human serum albumin. In some embodiments, the human serum albumin contains no more than 0.001 moles of fatty acids bound to one mole of human serum albumin. In some embodiments, the human serum albumin contains no more than 0.0005 moles of fatty acids bound to one mole of human serum albumin. In some embodiments, the human serum albumin contains no more than 0.0001 moles of fatty acids bound to one mole of human serum albumin.

In some embodiments, the cabozantinib can be a pharmaceutically acceptable salt of cabozantinib. In some embodiments, cabozantinib is a malate salt of cabozantinib. In some embodiments, cabozantinib is a (S)-malate salt of cabozantinib. In some embodiments, cabozantinib can be any one of crystal forms, amorphous forms, solvates and hydrates as described herein.

In some embodiments, the composition is a clear aqueous solution when the composition is dissolved in an aqueous solution. In some embodiments, the aqueous solution is substantially free of solvent other than water. In some embodiments, the aqueous solution is free of solvent other than water.

In some embodiments, the composition is a clear aqueous solution when the composition is dissolved in water. In some embodiments, the composition is a clear aqueous solution when the composition is dissolved in 0.9% saline solution. In some embodiments, the composition is a clear aqueous solution when the composition is dissolved in 5% Dextrose water solution.

As used herein, the term "aqueous solution" refers to a solution, wherein at least one solvent is water and the weight % of water in the mixture of solvents is at least 50%, at least 60%, at least 70% or at least 90%. In some embodiments, aqueous solution is a solution in which water is the only solvent. In some embodiments, aqueous solution is 0.9% saline solution. In some embodiments, aqueous solution is 5% Dextrose water solution. In some embodiments, aqueous solution is a buffer (e.g., phosphate buffer or a carbonate buffer). In some embodiments, the buffer is physiological buffer or a pharmaceutically acceptable buffer. In some embodiments, the buffer is any one of buffers described, for example, in Y.-C. Lee et al. International Journal of Pharmaceutics 253 (2003) 111-119, the disclosure of which is incorporated herein by reference in its entirety. In some embodiments, the buffer comprises maleic acid, tartaric acid, lactic acid, citric acid, acetic acid, sodium bicarbonate, sodium phosphate, or mixtures thereof. In some embodiments, the pH range of the buffer is from about 3 to about 9, from about 4 to about 8, from about 5 to about 7, from about 6 to about 7, from about 3 to about 5, from about 3 to about 7, from about 4 to about 6, or from about 6 to about 6. In some embodiments, the pH of the buffer is about 4, about 5, about 6, about 6.4, about 6.5, about 6.6, about 7, about 7.5, or about 8.

As used herein, the term "aqueous solvent" refer to a liquid comprising at least 50%, at least 60%, at least 70%, at least 90% or at least 95% water. In some embodiments, aqueous solvent is water.

As used herein, "substantially free of solvent," in reference to an aqueous solution, refers to an aqueous solution that contains less than 0.5%, by weight, of any non-water solvent. In some embodiments, the aqueous solution contains less than 0.1%, by weight, of any non-water solvent. In some embodiments, the aqueous solution contains less than 0.05%, by weight, of any non-water solvent.

As used herein, the term "clear aqueous solution" refers to a solution containing cabozantinib and HSA in an aqueous solution that is transparent upon visual observation and essentially free of visible particles or precipitation of undissolved cabozantinib.

The term "essentially free of visible particles or precipitation of undissolved cabozantinib" can be assessed as follows: after a clear aqueous solution is filtered with a 0.22 micron filter, the amount of cabozantinib in the filtered aqueous solution is at least 95% of the total amount of cabozantinib in the aqueous solution before filtration. The total amount of cabozantinib in the aqueous solution before filtration includes the particles or precipitation of undissolved cabozantinib in the aqueous solution or with the aqueous solution. The amount of the cabozantinib in an aqueous solution can be measured by the methods using HPLC. The methods of measuring the amount of the cabozantinib in an aqueous solution are illustrated in the experimental examples described herein. The methods are commonly understood by one of ordinary skill in the art to which this disclosure belongs.

When visually observed, for example, the term "clear aqueous solution" excludes a milky aqueous solution. Further, the term "clear aqueous solution" excludes a cloudy or hazy aqueous solution.

As used herein, the term "micron" refers to a unit of measure of one one-thousandth of a millimeter. In some embodiments, the term "micron" refers to a micrometer.

In some embodiments, the composition forms a clear aqueous solution, when the composition is dissolved in an aqueous solution, wherein the clear aqueous solution has pH value from about 5 to about 8. In some embodiments, the composition forms a clear aqueous solution, when the composition is dissolved in an aqueous solution, wherein the clear aqueous solution has pH value from about 5.5 to about 7.8. In some embodiments, the composition forms a clear aqueous solution, when the composition is dissolved in an aqueous solution, wherein the clear aqueous solution has pH value from about 6 to about 7.5. In some embodiments, the composition forms a clear aqueous solution, when the composition is dissolved in an aqueous solution, wherein the clear aqueous solution has pH value from about 6.5 to about 7.5. In some embodiments, the composition forms a clear aqueous solution, when the composition is dissolved in an aqueous solution, wherein the clear aqueous solution has pH value from about 6 to about 6.5. In some embodiments, the composition forms a clear aqueous solution, when the composition is dissolved in an aqueous solution, wherein the clear aqueous solution has pH value from about 6.5 to about 7. In some embodiments, the composition forms a clear aqueous solution, when the composition is dissolved in an aqueous solution, wherein the clear aqueous solution has pH value from about 7 to about 7.5. In some embodiments, the composition forms a clear aqueous solution, when the composition is dissolved in an aqueous solution, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous solution is substantially free of solvent other than water. In some embodiments, the aqueous solution is free of solvent other than water.

In some embodiments, the composition forms a clear aqueous solution, when the composition is dissolved in water, wherein the clear aqueous solution has pH value from about 5 to about 8. In some embodiments, the composition forms a clear aqueous solution, when the composition is dissolved in water, wherein the clear aqueous solution has pH value from about 5.5 to about 7.8. In some embodiments, the composition forms a clear aqueous solution, when the composition is dissolved in water, wherein the clear aqueous solution has pH value from about 6 to about 7.5. In some embodiments, the composition forms a clear aqueous solution, when the composition is dissolved in water, wherein the clear aqueous solution has pH value from about 6.5 to about 7.5. In some embodiments, the composition forms a clear aqueous solution, when the composition is dissolved in water, wherein the clear aqueous solution has pH value from about 6 to about 6.5. In some embodiments, the composition forms a clear aqueous solution, when the composition is dissolved in water, wherein the clear aqueous solution has pH value from about 6.5 to about 7. In some embodiments, the composition forms a clear aqueous solution, when the composition is dissolved in water, wherein the clear aqueous solution has pH value from about 7 to about 7.5. In some embodiments, the composition forms a clear aqueous solution, when the composition is dissolved in water, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

In some embodiments, the composition forms a clear aqueous solution, when the composition is dissolved in 0.9% saline solution, wherein the clear aqueous solution has pH value from about 5 to about 8. In some embodiments, the composition forms a clear aqueous solution, when the composition is dissolved in 0.9% saline solution, wherein the clear aqueous solution has pH value from about 5.5 to about 7.8. In some embodiments, the composition forms a clear aqueous solution, when the composition is dissolved in 0.9% saline solution, wherein the clear aqueous solution has pH value from about 6 to about 7.5. In some embodiments, the composition forms a clear aqueous solution, when the composition is dissolved in 0.9% saline solution, wherein the clear aqueous solution has pH value from about 6.5 to about 7.5. In some embodiments, the composition forms a clear aqueous solution, when the composition is dissolved in 0.9% saline solution, wherein the clear aqueous solution has pH value from about 6 to about 6.5. In some embodiments, the composition forms a clear aqueous solution, when the composition is dissolved in 0.9% saline solution, wherein the clear aqueous solution has pH value from about 6.5 to about 7. In some embodiments, the composition forms a clear aqueous solution, when the composition is dissolved in 0.9% saline solution, wherein the clear aqueous solution has pH value from about 7 to about 7.5. In some embodiments, the composition forms a clear aqueous solution, when the composition is dissolved in 0.9% saline solution, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

In some embodiments, the composition forms a clear aqueous solution, when the composition is dissolved in 5% Dextrose water solution, wherein the clear aqueous solution has pH value from about 5 to about 8. In some embodiments, the composition forms a clear aqueous solution, when the composition is dissolved in 5% Dextrose water solution, wherein the clear aqueous solution has pH value from about 5.5 to about 7.8. In some embodiments, the composition forms a clear aqueous solution, when the composition is dissolved in 5% Dextrose water solution, wherein the clear aqueous solution has pH value from about 6 to about 7.5. In some embodiments, the composition forms a clear aqueous solution, when the composition is dissolved in 5% Dextrose water solution, wherein the clear aqueous solution has pH value from about 6.5 to about 7.5. In some embodiments, the composition forms a clear aqueous solution, when the composition is dissolved in 5% Dextrose water solution, wherein the clear aqueous solution has pH value from about 6 to about 6.5. In some embodiments, the composition forms a clear aqueous solution, when the composition is dissolved in 5% Dextrose water solution, wherein the clear aqueous solution has pH value from about 6.5 to about 7. In some embodiments, the composition forms a clear aqueous solution, when the composition is dissolved in 5% Dextrose water solution, wherein the clear aqueous solution has pH value from about 7 to about 7.5. In some embodiments, the composition forms a clear aqueous solution, when the composition is dissolved in 5% Dextrose water solution, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

In some embodiments, the composition is a clear aqueous solution when the composition is dissolved in an aqueous solvent (e.g. Water, 0.9% saline solution, or 5% Dextrose water solution), wherein after the clear aqueous solution is filtered by a 0.22 micron filter after a time period selected from 1 hour, 2 hours, 3 hours, 4 hours, 5 hours and 24 hours, the amount of cabozantinib in the filtered aqueous solution is at least 96% of the total amount of cabozantinib in the aqueous solution at the time of dissolution before the filtration. In some embodiments, the composition is a clear aqueous solution when the composition is dissolved in an aqueous solvent (e.g. Water, 0.9% saline solution, or 5% Dextrose water solution), wherein after the clear aqueous solution is filtered by a 0.22 micron filter after a time period selected from 1 hour, 2 hours, 3 hours, 4 hours, 5 hours and 24 hours, the amount of cabozantinib in the filtered aqueous solution is at least 97% of the total amount of cabozantinib in the aqueous solution at the time of dissolution before the filtration. In some embodiments, the composition is a clear aqueous solution when the composition is dissolved in an aqueous solution (e.g. Water, 0.9% saline solution, or 5% Dextrose water solution), wherein after the clear aqueous solution is filtered by a 0.22 micron filter after a time period selected from 1 hour, 2 hours, 3 hours, 4 hours, 5 hours and 24 hours, the amount of cabozantinib in the filtered aqueous solution is at least 98% of the total amount of cabozantinib in the aqueous solution at the time of dissolution before the filtration. In some embodiments, the composition is a clear aqueous solution when the composition is dissolved in an aqueous solution (e.g. Water, 0.9% saline solution, or 5% Dextrose water solution), wherein after the clear aqueous solution is filtered by a 0.22 micron filter after a time period selected from 1 hour, 2 hours, 3 hours, 4 hours, 5 hours and 24 hours, the amount of cabozantinib in the filtered aqueous solution is at least 99% of the total amount of cabozantinib in the aqueous solution at the time of dissolution before the filtration. In some embodiments, the composition is a clear aqueous solution when the composition is dissolved in an aqueous solution (e.g. Water, 0.9% saline solution, or 5%

Dextrose water solution), wherein after the clear aqueous solution is filtered by a 0.22 micron filter after a time period selected from 1 hour, 2 hours, 3 hours, 4 hours, 5 hours and 24 hours, the amount of cabozantinib in the filtered aqueous solution is at least 99.5% of the total amount of cabozantinib in the aqueous solution at the time of dissolution before the filtration. In some embodiments, the aqueous solution is free of solvent other than water. In some embodiments, the aqueous solution is substantially free of solvent other than water.

In some embodiments, the amount of cabozantinib that is bound to the HSA (e.g., non-covalently) in the aqueous solution (e.g., clear aqueous solution) comprising the composition comprising cabozantinib and HSA (as described herein) is at least 40%, at least 50%, at least 60%, at least 70%, at least 80%, at least 90%, at least 95%, at least 99%, or about 100% of the total about of cabozantinib in the aqueous solution.

In some embodiments, the composition is an aqueous solution, wherein after the aqueous solution is filtered by a 0.22 micron filter after a time period selected from 1 hour, 2 hours, 3 hours, 4 hours, 5 hours and 24 hours, the amount of cabozantinib in the filtered aqueous solution is at least 80% of the total amount of cabozantinib in the aqueous solution at the time of dissolution before the filtration. In some embodiments, the composition is an aqueous solution, wherein after the aqueous solution is filtered by a 0.22 micron filter after a time period selected from 1 hour, 2 hours, 3 hours, 4 hours, 5 hours and 24 hours, the amount of cabozantinib in the filtered aqueous solution is at least 85% of the total amount of cabozantinib in the aqueous solution at the time of dissolution before the filtration. In some embodiments, the composition is an aqueous solution, wherein after the aqueous solution is filtered by a 0.22 micron filter after a time period selected from 1 hour, 2 hours, 3 hours, 4 hours, 5 hours and 24 hours, the amount of cabozantinib in the filtered aqueous solution is at least 90% of the total amount of cabozantinib in the aqueous solution at the time of dissolution before the filtration. In some embodiments, the aqueous solution is free of solvent other than water. In some embodiments, the aqueous solution is substantially free of solvent other than water.

In some embodiments, the composition is a clear aqueous solution for at least 1 hour when the composition is dissolved in an aqueous solution. In some embodiments, the composition is a clear aqueous solution for at least 2 hours when the composition is dissolved in an aqueous solution. In some embodiments, the composition is a clear aqueous solution for at least 3 hours when the composition is dissolved in an aqueous solution. In some embodiments, the composition is a clear aqueous solution for at least 4 hours when the composition is dissolved in an aqueous solution. In some embodiments, the composition is a clear aqueous solution for at least 5 hours when the composition is dissolved in an aqueous solution. In some embodiments, the composition is a clear aqueous solution for at least 6 hours when the composition is dissolved in an aqueous solution. In some embodiments, the composition is a clear aqueous solution for at least 8 hours when the composition is dissolved in an aqueous solution. In some embodiments, the composition is a clear aqueous solution for at least 24 hours when the composition is dissolved in an aqueous solution. In some embodiments, the aqueous solution is substantially free of solvent other than water. In some embodiments, the aqueous solution free of solvent other than water.

In some embodiments, the composition is a solid formulation. For example, the solid formulation can be produced in a uniform manner by lyophilization. A skilled artisan would recognize other methods, such as rotary evaporation, that can also produce solid formulations.

In some embodiments, the composition is an aqueous formulation. In some embodiments, the aqueous formulation is substantially free of solvent other than water. In some embodiments, the aqueous formulation is free of solvent other than water.

In some embodiments, the aqueous formulation can be free of a surfactant, such as CREMOPHOR® surfactants and Polysorbate 80. In some embodiments, the aqueous formulation can be substantially free of a surfactant, such as CREMOPHOR® surfactants and Polysorbate 80. In some embodiments, the aqueous formulation can be substantially free of a surfactant selected from the group consisting of CREMOPHOR® surfactants and Polysorbate 80.

As used herein, the term "substantially free of surfactant" refers to a formulation containing less than 0.0005%, less than 0.0003%, or less than 0.0001% of surfactants and/or less than 0.0005%, less than 0.0003%, or less than 0.0001% of surfactant.

In some embodiments, the aqueous formulation is a clear aqueous solution. For example, the formulation can be a clear and stable aqueous solution reconstituted from a sterile lyophilized powder. In some embodiments, the aqueous formulation is a clear aqueous solution, wherein the aqueous formulation is substantially free of solvent other than water. In some embodiments, the aqueous formulation is a clear aqueous solution, wherein the aqueous formulation is free of solvent other than water.

In some embodiments, the aqueous formulation is a clear aqueous solution reconstituted from the solid formulation (e.g. the sterile lyophilized powder) in water. In some embodiments, the aqueous formulation is a clear aqueous solution reconstituted from the solid formulation (e.g. the sterile lyophilized powder) in 0.9% saline solution. In some embodiments, the aqueous formulation is a clear aqueous solution reconstituted from the solid formulation (e.g. the sterile lyophilized powder) in 5% Dextrose water solution.

In some embodiments, the aqueous formulation has pH value from about 5 to about 8. In some embodiments, the aqueous formulation has pH value from about 5.5 to about 7.8. In some embodiments, the aqueous formulation has pH value from about 6 to about 7.5. In some embodiments, the aqueous formulation has pH value from about 6.5 to about 7.5. In some embodiments, the aqueous formulation has pH value from about 6 to about 6.5. In some embodiments, the aqueous formulation has pH value from about 6.5 to about 7. In some embodiments, the aqueous formulation has pH value from about 7 to about 7.5. In some embodiments, the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous formulation is substantially free of solvent other than water. In some embodiments, the aqueous formulation is free of solvent other than water.

In some embodiments, when the composition comprising cabozantinib and HSA as described herein (e.g., sterile solid powder) is dissolved in an aqueous solvent (e.g., water, saline or 5% dextrose), the resultant aqueous solution, when filtered using a 0.22 micron filter, comprises at least 99.8% at the time of preparation, at least 99.4% after 1 hour, at least 98.7% after 2 hours, at least 98.2% after 3 hours, at least 98% after 4 hours, at least 97.6% after 5 hours, at least 97.3% after 6 hours, or at least 96.4% after 24 hours of the amount of cabozantinib used to prepare the composition.

In some embodiments, when the composition comprising cabozantinib and HSA as described herein (e.g., sterile solid powder) is dissolved in an aqueous solvent (e.g., water, saline or 5% dextrose), the resultant aqueous solution, when filtered using a 0.22 micron filter, comprises at least 99.8% at the time of preparation, at least 99.8% after 1 hour, at least 99.6% after 2 hours, at least 99.3% after 3 hours, at least 99.1% after 4 hours, at least 98.9% after 5 hours, at least 98.7% after 6 hours, or at least 96.7% after 24 hours of the amount of cabozantinib used to prepare the composition.

In some embodiments, when the composition comprising cabozantinib and HSA as described herein (e.g., sterile solid powder) is dissolved in an aqueous solvent (e.g., water, saline or 5% dextrose), the resultant aqueous solution, when filtered using a 0.22 micron filter, comprises at least 99% at the time of preparation, at least 99% after 1 hour, at least 98% after 2 hours, at least 98% after 3 hours, at least 98% after 4 hours, at least 97% after 5 hours, at least 97% after 6 hours, or at least 96% after 24 hours of the amount of cabozantinib used to prepare the composition.

In some embodiments, when the composition comprising cabozantinib and HSA as described herein (e.g., sterile solid powder) is dissolved in an aqueous solvent (e.g., water, saline or 5% dextrose), the resultant aqueous solution, when filtered using a 0.22 micron filter, comprises at least 95% at the time of preparation, at least 95% after 1 hour, at least 95% after 2 hours, at least 95% after 3 hours, at least 95% after 4 hours, at least 95% after 5 hours, or at least 95% after 6 hours of the amount of cabozantinib used to prepare the composition.

In some embodiments, when the composition comprising cabozantinib and HSA as described herein (e.g., sterile solid powder) is dissolved in an aqueous solvent (e.g., water, saline or 5% dextrose), the resultant aqueous solution, when filtered using a 0.22 micron filter, comprises at least 96% at the time of preparation, at least 96% after 1 hour, at least 96% after 2 hours, at least 96% after 3 hours, at least 96% after 4 hours, at least 96% after 5 hours, or at least 96% after 6 hours of the amount of cabozantinib used to prepare the composition.

In some embodiments, when the composition comprising cabozantinib and HSA as described herein (e.g., sterile solid powder) is dissolved in an aqueous solvent (e.g., water, saline or 5% dextrose), the resultant aqueous solution, when filtered using a 0.22 micron filter, comprises at least 95% at the time of preparation, at least 97% after 1 hour, at least 97% after 2 hours, at least 97% after 3 hours, at least 97% after 4 hours, at least 97% after 5 hours, or at least 97% after 6 hours of the amount of cabozantinib used to prepare the composition.

In some embodiments, when the composition comprising cabozantinib and HSA as described herein (e.g., sterile solid powder) is dissolved in an aqueous solvent (e.g., water, saline or 5% dextrose), the resultant aqueous solution, when filtered using a 0.22 micron filter, comprises at least 98% at the time of preparation, at least 98% after 1 hour, at least 98% after 2 hours, at least 98% after 3 hours, at least 98% after 4 hours, at least 98% after 5 hours, or at least 98% after 6 hours of the amount of cabozantinib used to prepare the composition.

In some embodiments, when the composition comprising cabozantinib and HSA as described herein (e.g., sterile solid powder) is dissolved in an aqueous solvent (e.g., water, saline or 5% dextrose), the resultant aqueous solution, when filtered using a 0.22 micron filter, comprises at least 99% at the time of preparation, at least 99% after 1 hour, at least 99% after 2 hours, at least 99% after 3 hours, at least 99% after 4 hours, at least 99% after 5 hours, or at least 99% after 6 hours of the amount of cabozantinib used to prepare the composition.

In some embodiments, the aqueous formulation is a clear aqueous solution for at least 1 hour. In some embodiments, the aqueous formulation is a clear aqueous solution for at least 1 hour at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 2 hours. In some embodiments, the aqueous formulation is a clear aqueous solution for at least 2 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 3 hours. In some embodiments, the aqueous formulation is a clear aqueous solution for at least 3 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 6 hours. In some embodiments, the aqueous formulation is a clear aqueous solution for at least 6 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 24 hours. In some embodiments, the aqueous formulation is a clear aqueous solution for at least 24 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 3 days. In some embodiments, the aqueous formulation is a clear aqueous solution for at least 3 days when dissolved in an aqueous solution at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least about 1 hour, 2 hours, 3 hours, 4 hours, 5 hours, 6 hours, 8 hours, or 24 hours. In some embodiments, the aqueous formulation is substantially free of solvent other than water. In some embodiments, the aqueous formulation is free of solvent other than water.

In some embodiments, after the aqueous formulation is filtered by a 0.22 micron filter, the amount of cabozantinib in the filtered aqueous solution is at least 96% of the total amount of cabozantinib in the aqueous solution before the filtration. In some embodiments, after the aqueous formulation is filtered by a 0.22 micron filter, the amount of cabozantinib in the filtered aqueous solution is at least 97% of the total amount of cabozantinib in the aqueous solution before the filtration. In some embodiments, after the aqueous formulation is filtered by a 0.22 micron filter, the amount of cabozantinib in the filtered aqueous solution is at least 98% of the total amount of cabozantinib in the aqueous solution before the filtration. In some embodiments, after the aqueous formulation is filtered by a 0.22 micron filter, the amount of cabozantinib in the filtered aqueous solution is at least 99% of the total amount of cabozantinib in the aqueous solution before the filtration. In some embodiments, after the aqueous formulation is filtered by a 0.22 micron filter, the amount of cabozantinib in the filtered aqueous solution is at least 99.5% of the total amount of cabozantinib in the aqueous solution before the filtration. In some aspects of these embodiments, the aqueous formulation is filtered by a 0.22-micron filter at a time period selected from 1 hour, 2 hours, 3, hours, 4 hours, 5 hours, 6 hours, 12 hours, 18 hours and 24 hours. In some embodiments, the aqueous formulation is free of solvent other than water. In some embodiments, the aqueous formulation is substantially free of solvent other than water.

In some embodiments, after the aqueous formulation (e.g. a clear aqueous solution) is filtered by a 0.22 micron filter, the amount of cabozantinib in the filtered aqueous solution is at least 96%, 97%, 98%, 99%, or 99.5% of the total amount of cabozantinib in the aqueous solution before filtration, wherein the clear aqueous solution has pH value from about 5 to about 8, and wherein the clear aqueous solution is substantially free of solvent other than water. In some embodiments, after the aqueous formulation (e.g. a clear aqueous solution) is filtered by a 0.22 micron filter, the amount of cabozantinib in the filtered aqueous solution is at least 96%, 97%, 98%, 99%, or 99.5% of the total amount of cabozantinib in the aqueous solution before filtration, wherein the clear aqueous solution has pH value from about 6 to about 7.5, and wherein the clear aqueous solution is substantially free of solvent other than water. In some embodiments, after the aqueous formulation (e.g. a clear aqueous solution) is filtered by a 0.22 micron filter, the amount of cabozantinib in the filtered aqueous solution is at least 96%, 97%, 98%, 99%, or 99.5% of the total amount of cabozantinib in the aqueous solution before filtration, wherein the clear aqueous solution has pH value from about 5 to about 8, and wherein the clear aqueous solution is free of solvent other than water. In some embodiments, after the aqueous formulation (e.g. a clear aqueous solution) is filtered by a 0.22 micron filter, the amount of cabozantinib in the filtered aqueous solution is at least 96%, 97%, 98%, 99%, or 99.5% of the total amount of cabozantinib in the aqueous solution before filtration, wherein the clear aqueous solution has pH value from about 6 to about 7.5, and wherein the clear aqueous solution is free of solvent other than water. n some aspects of these embodiments, the aqueous formulation is filtered by a 0.22-micron filter at a time period selected from 1 hour, 2 hours, 3, hours, 4 hours, 5 hours, 6 hours, 12 hours, 18 hours and 24 hours.

In some embodiments, after the aqueous formulation is filtered by a 0.22 micron filter, the amount of cabozantinib in the filtered aqueous solution is at least 80% of the total amount of cabozantinib in the aqueous solution before the filtration. In some embodiments, after the aqueous formulation is filtered by a 0.22 micron filter, the amount of cabozantinib in the filtered aqueous solution is at least 85% of the total amount of cabozantinib in the aqueous solution before the filtration. In some embodiments, after the aqueous formulation is filtered by a 0.22 micron filter, the amount of cabozantinib in the filtered aqueous solution is at least 90% of the total amount of cabozantinib in the aqueous solution before the filtration. In some aspects of these embodiments, the aqueous formulation is filtered by a 0.22-micron filter at a time period selected from 1 hour, 2 hours, 3, hours, 4 hours, 5 hours, 6 hours, 12 hours, 18 hours and 24 hours. In some embodiments, the aqueous formulation is free of solvent other than water. In some embodiments, the aqueous formulation is substantially free of solvent other than water.

Also, provided herein is a pharmaceutical composition comprising the composition comprising the cabozantinib and the human serum albumin as described herein, and a pharmaceutically acceptable carrier.

In some embodiments, the pharmaceutical composition further comprises at least one anti-cancer drug (e.g., any one of the anti-cancer drugs as described herein).

As used herein, the term "pharmaceutically acceptable carrier" is meant any solution used to solubilize and deliver an agent to a subject. A desirable pharmaceutically acceptable carrier is saline. Other pharmaceutically acceptable carrier and their formulation are known to one skilled in the art and described, for example, in Remington's Pharmaceutical Sciences. (20$^{th}$ edition), ed. A. Gennaro, 2003, Lippincon Williams & Wilkins.

Pharmaceutically acceptable carriers that may be used in the pharmaceutical compositions of the present application include, but are not limited to, ion exchangers, alumina, aluminum stearate, lecithin, serum proteins (other than HSA), buffer substances such as phosphates, glycine, sorbic acid, potassium sorbate, salts or electrolytes, such as protamine sulfate, disodium hydrogen phosphate, potassium hydrogen phosphate, sodium chloride, zinc salts, colloidal silica, magnesium trisilicate, and cellulose-based substances.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

In some embodiments, the pharmaceutical composition is free of a surfactant, such as CREMOPHOR® surfactants and Polysorbate 80. In some embodiments, the pharmaceutical composition is substantially free of a surfactant, such as CREMOPHOR® surfactants and Polysorbate 80. In some embodiments, the pharmaceutical composition can be substantially free of a surfactant selected from the group consisting of CREMOPHOR® surfactants and Polysorbate 80.

Also, provided herein is a method of treating a proliferative disease comprising the step of administering to a subject in need thereof a pharmaceutical composition comprising the composition comprising the cabozantinib and the human serum albumin as described herein, and a pharmaceutically acceptable carrier.

As used herein, the terms "individual", "patient", or "subject" are used interchangeably and refer to any animal, including mammals, preferably mice, rats, other rodents, rabbits, dogs, cats, swine, cattle, sheep, horses, or primates, and most preferably humans.

As used herein, the term "proliferative disease" refers to a disease caused by excessive proliferation of cells and turnover of cellular matrix. Non-limiting examples of proliferative diseases include cancer, atherosclerosis, arthritis (e.g. rheumatoid arthritis), psoriasis, fibrosis (e.g. pulmonary fibrosis, idiopathic pulmonary fibrosis), scleroderma and cirrhosis (e.g. cirrhosis of the liver).

Also, provided herein is a method of treating a cancer (e.g., any one of cancers described herein), the method comprising the step of administering to a subject in need thereof of a therapeutically effective amount of a pharmaceutical composition comprising the composition comprising the cabozantinib and the human serum albumin as described herein, and a pharmaceutically acceptable carrier.

In some embodiments, cancer is selected from sarcoma, angiosarcoma, fibrosarcoma, rhabdomyosarcoma, liposarcoma, myxoma, rhabdomyoma, fibroma, lipoma, teratoma, non-small cell lung cancer (NSCLC), bronchogenic carcinoma squamous cell, undifferentiated small cell, undifferentiated large cell, adenocarcinoma, alveolar bronchiolar carcinoma, bronchial adenoma, sarcoma, lymphoma, chondromatous hamartoma, mesothelioma, gastrointestinal cancer, cancer of the esophagus, squamous cell carcinoma, adenocarcinoma, leiomyosarcoma, lymphoma, cancer of the stomach, carcinoma, lymphoma, leiomyosarcoma, cancer of the pancreas, ductal adenocarcinoma, insulinoma, glucagonoma, gastrinoma, carcinoid tumor, vipoma, cancer of the small bowel, adenocarcinoma, lymphoma, carcinoid tumors, Kaposi's sarcoma, leiomyoma, hemangioma, lipoma, neurofibroma, fibroma, cancer of the large bowel or colon, tubular adenoma, villous adenoma, hamartoma, leiomyoma, genitourinary tract cancer, cancer of the kidney adenocarcinoma, Wilm's tumor (nephroblastoma), lymphoma, leukemia, cancer of the bladder, cancer of the urethra, squamous cell carcinoma, transitional cell carcinoma, cancer of the prostate, cancer of the testis, seminoma, teratoma, embryonal carcinoma, teratocarcinoma, choriocarcinoma, sarcoma, interstitial cell carcinoma, fibroma, fibroadenoma, adenomatoid tumors, lipoma, liver cancer, hepatoma hepatocellular carcinoma, cholangiocarcinoma, hepatoblastoma, angiosarcoma, hepatocellular adenoma, hemangioma, bone cancer, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochrondroma (osteocartilaginous exostoses), benign chondroma, chondroblastoma, chondromyxofibroma, osteoid osteoma giant cell tumor, nervous system cancer, cancer of the skull, osteoma, hemangioma, granuloma, xanthoma, osteitis deformans, cancer of the meninges meningioma, meningiosarcoma, gliomatosis, cancer of the brain, astrocytoma, medulloblastoma, glioma, ependymoma, germinoma (pinealoma), glioblastoma multiforme, oligodendroglioma, schwannoma, retinoblastoma, congenital tumors, cancer of the spinal cord, neurofibroma, meningioma, glioma, sarcoma, gynecological cancer, cancer of the uterus, endometrial carcinoma, cancer of the cervix, cervical carcinoma, pre tumor cervical dysplasia, cancer of the ovaries, ovarian carcinoma, serous cystadenocarcinoma, mucinous cystadenocarcinoma, unclassified carcinoma, granulosa-theca cell tumor, Sertoli Leydig cell tumor, dysgerminoma, malignant teratoma, cancer of the vulva, squamous cell carcinoma, intraepithelial carcinoma, adenocarcinoma, fibrosarcoma, melanoma, cancer of the vagina, clear cell carcinoma, squamous cell carcinoma, botryoid sarcoma, embryonal rhabdomyosarcoma, cancer of the fallopian tubes, hematologic cancer, cancer of the blood, acute myeloid leukemia (AML), chronic myeloid leukemia (CML), acute lymphoblastic leukemia (ALL), chronic lymphoblastic leukemia, chronic lymphocytic leukemia, myeloproliferative diseases, multiple myeloma, myelodysplastic syndrome, Hodgkin's lymphoma, non-Hodgkin's lymphoma (malignant lymphoma), Waldenstrom's macroglobulinemia, skin cancer, malignant melanoma, basal cell carcinoma, squamous cell carcinoma, Kaposi's sarcoma, moles dysplastic nevi, lipoma, angioma, dermatofibroma, keloids, psoriasis, adrenal gland cancer, and neuroblastoma.

As used herein, an "effective amount," "therapeutically effective amount," or a "pharmaceutically-effective amount" in reference to the compounds or compositions of the instant invention refers to the amount sufficient to induce a desired biological, pharmacological, or therapeutic outcome in a subject. That result can be reduction, mitigation, delay, shortening the time to resolution of, alleviation of the signs or symptoms of, or exert a medically-beneficial effect upon the underlying pathophysiology or pathogenesis of an expected or observed side-effect, toxicity, disorder or condition, or any other desired alteration of a biological system. In cancer treatment, the result will generally include the reduction, mitigation, limitation, and/or, delay of the deleterious physiological manifestations, growth or metastases of neoplasms.

In some embodiments, the cancer is a solid tumor. In some embodiments, the cancer is selected from the group consisting of thyroid cancer, renal cell carcinoma (RCC), kidney cancer, hepatocellular cancer, non-small cell lung cancer, ovarian cancer, glioblastoma, melanoma, and colorectal cancer. In some embodiments, the cancer is a thyroid cancer. In some embodiments, the cancer is a metastatic medullary thyroid cancer. In some embodiments, the cancer is a renal cell carcinoma (RCC). In some embodiments, the cancer is an advanced renal cell carcinoma (RCC) who have received prior antiangiogenic therapy. In some embodiments, the cancer is an advanced renal cell carcinoma. In some embodiments the cancer is a kidney cancer. In some embodiments, the cancer is a hepatocellular cancer. In some embodiments, the cancer is a non-small cell lung cancer. In some embodiments, the cancer is a ovarian cancer. In some embodiments, the cancer is a glioblastoma. In some embodiments, the cancer is a melanoma. In some embodiments, the cancer is a colorectal cancer.

In some embodiments, the method of treating cancer (e.g., any one of cancers described herein) comprises the step of administering to a subject in need thereof a therapeutically effective amount of a pharmaceutical composition comprising the composition comprising the cabozantinib and the human serum albumin as described herein, and a therapeutically effective amount of at least one inhibitor of the following kinases for the treatment of cancer: PIM, Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf.

In some embodiments, the method of treating cancer (e.g. any one of cancers described herein) comprises the step of administering to a subject in need thereof a therapeutically effective amount of a pharmaceutical composition comprising the composition comprising the cabozantinib and the human serum albumin as described herein, and a therapeutically effective amount of at least one anti-cancer drug. Examples of an anti-cancer drug include aberaterone, aberaterone acetate, abarelix, aldesleukin, alemtuzumab, alitretinoin, allopurinol, altretamine, anastrozole, arsenic trioxide, asparaginase, azacitidine, bavituximab, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, enzalutamide, epirubicin, erlotinib, vemurafenib, pilimumab, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

In some embodiments, the anti-cancer drug is an antibody useful in treating cancer. In some embodiments, the antibody useful in treating cancer is abagovomab, adecatumumab, afutuzumab, alacizumab pegol, altumomab pentetate, amatuximab, anatumomab mafenatox, apolizumab, arcitumomab, bavituximab, bectumomab, belimumab, bevacizumab, bivatuzumab mertansine, blinatumomab, brentuximab vedotin, cantuzumab mertansine, cantuzumab ravtansine, capromab pendetide, cetuximab, citatuzumab bogatox, cixutumumab, clivatuzumab tetraxetan, dacetuzumab, demcizumab, detumomab, drozitumab, ecromeximab, eculizumab, elotuzumab, ensituximab, epratuzumab, etaracizumab, farletuzumab, figitumumab, flanvotumab, galiximab, gemtuzumab ozogamicin, girentuximab, ibritumomab tiuxetan, imgatuzumab, ipilimumab, labetuzumab, lexatumumab, lorvotuzumab mertansine, nimotuzumab, ofatumumab, oregovomab, panitumumab, pemtumomab, pertuzumab, tacatuzumab tetraxetan, tositumomab, trastuzumab, totumumab, or zalutumumab.

In some embodiments, a composition comprising the cabozantinib and the human serum albumin as described herein and an anti-cancer drug are administered simultaneously.

In some embodiments, a composition comprising the cabozantinib and the human serum albumin as described herein and an anti-cancer drug are administered consecutively.

The composition comprising the cabozantinib and the human serum albumin described herein can be administered to an individual, such as human, via various routes, such as parenterally, including intravenous (e.g., as an infusion), intra-arterial, intraperitoneal, intrapulmonary, oral, inhalation, intravesicular, intramuscular, intra-tracheal, subcutaneous, intraocular, intrathecal, or transdermal. For example, the composition can be administered by inhalation to treat conditions of the respiratory tract. The composition can be used to treat respiratory conditions such as pulmonary fibrosis, broncheolitis obliterans, lung cancer, bronchoalveolar carcinoma, and the like. In some embodiments, the composition is administrated intravenously.

The methods described herein may be performed alone or in conjunction with another therapy, such as surgery, radiation, chemotherapy, immunotherapy, gene therapy, and the like. Additionally, a person having a greater risk of developing the proliferative disease may receive treatments to inhibit or and/or delay the development of the disease.

As will be understood by those of ordinary skill in the art, the appropriate doses of cabozantinib will be approximately those already employed in clinical therapies wherein cabozantinib is administered alone or in combination with other chemotherapeutic agents. Variation in dosage will likely occur depending on the condition being treated. Appropriate effective doses will also vary, as recognized by those skilled in the art, depending on the severity of the disease, the route of administration, the sex, age and general health condition of the subject, excipient usage, the possibility of co-usage with other therapeutic treatments such as use of other agents, and the judgment of the treating physician. For example, guidance for selecting an effective dose can be determined by reference to the prescribing information for cabozantinib (COMETRIQ or CABOMETYX), which are incorporated herein by reference in its entirety. In some embodiments, a pharmaceutical composition comprising the composition of cabozantinib and HSA as described herein is administered orally (e.g., once daily) and the effective amount of cabozantinib in the pharmaceutical composition is from about 60 mg to about 140 mg. In some embodiments, the effective amount of cabozantinib in the pharmaceutical composition is about 140 mg. In some embodiments, the effective amount of cabozantinib in the pharmaceutical composition is about 60 mg. In some embodiments, a pharmaceutical composition comprising the composition of cabozantinib and HSA as described herein is administered to the subject (e.g., by injection and/or infusion) such that the subject receives from about 60 mg/day to about 140 mg/day of cabozantinib. In some embodiments, a pharmaceutical composition comprising the composition of cabozantinib and HSA as described herein is administered to the subject (e.g., by injection and/or infusion) such that the subject receives about 60 mg/day or about 140 mg/day of cabozantinib.

Also, provided herein is a liquid pharmaceutical composition comprising the composition comprising the cabozantinib and the human serum albumin as described herein, and a pharmaceutically acceptable carrier.

In some embodiments, the liquid pharmaceutical composition is a reconstituted solution, reconstituted from the solid composition comprising the cabozantinib and the human serum albumin as described herein.

In some embodiments, the liquid pharmaceutical composition is an aqueous solution. In some embodiments, the liquid pharmaceutical composition is an aqueous solution substantially free of solvent other than water. In some embodiments, the liquid pharmaceutical composition is an aqueous solution free of solvent other than water.

In some embodiments, the liquid pharmaceutical composition is an aqueous reconstituted solution, reconstituted in a parenterally acceptable aqueous pharmaceutical diluent. In some embodiments, the liquid pharmaceutical composition is an aqueous reconstituted solution, reconstituted in an aqueous infusion fluid.

In some embodiments, the liquid pharmaceutical composition is an injectable pharmaceutical formulation.

In some embodiments, the injectable pharmaceutical formulation is free of solvent other than water. In some embodiments, the injectable pharmaceutical formulation is substantially free of solvent other than water.

In some embodiments, the injectable pharmaceutical formulation is a reconstituted solution, reconstituted from the composition comprising the cabozantinib and the human serum albumin as described herein. In some embodiments, the injectable pharmaceutical formulation is a reconstituted solution, reconstituted in an aqueous infusion fluid. In some embodiments, the aqueous infusion fluid is normal saline. In some embodiments, the aqueous infusion fluid is a dextrose solution.

Also, provided herein is a composition consisting essentially of cabozantinib and human serum albumin, wherein the cabozantinib and the human serum albumin in the composition have a ratio by weight from about 1:5 to about 1:2000.

In some embodiments, the cabozantinib and the human serum albumin in the composition have a ratio by weight from about 1:100 to about 1:2000, from about 1:130 to about 1:1000, from about 1:130 to about 1:500, from about 1:140 to about 1:500, from about 1:150 to about 1:800, from about 1:150 to about 1:700, from about 1:150 to about 1:600, from about 1:150 to about 1:500, from about 1:150 to about 1:400, from about 1:150 to about 1:350, from about 1:150 to about 1:300, from about 1:160 to about 1:700, from about 1:160 to about 1:600, from about 1:160 to about 1:500, from about 1:160 to about 1:400, from about 1:160 to about 1:350, from about 1:160 to about 1:300, from about 1:165 to about 1:700, from about 1:165 to about 1:600, from about 1:165 to about 1:500, from about 1:165 to about 1:400, from about 1:165 to about 1:350, from about 1:165 to about 1:300, from about 1:170 to about 1:700, from about 1:170 to about 1:600, from about 1:170 to about 1:500, from about 1:170 to about 1:400, from about 1:170 to about 1:350, from about 1:170 to about 1:300, from about 1:150 to about 1:250, from about 1:160 to about 1:250, from about 1:165 to about 1:250, or from about 1:170 to about 1:250. In some embodiments, the cabozantinib and the human serum albumin have a ratio by weight of about 1:130, about 1:140, about 1:150, about 1:155, about 1:160, about 1:162.5, about 165, about 1:170, about 1:175, about 1:180, about 1:190, about 1:200, about 1:210, about 1:220, about 1:230, about 1:240, about 1:250, about 1:260, about 1:270, or about 1:280, about 1:290, about 1:300, about 1:350, about 1:400, or about 1:500.

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free. In some embodiments, the human serum albumin contains no more than two moles of fatty acids bound to one mole of human serum albumin. In some embodiments, the human serum albumin contains no more than one mole of fatty acids bound to one mole of human serum albumin. In some embodiments, human serum albumin contains no more than 0.5 moles of fatty acids bound to one mole of human serum albumin. In some embodiments, the human serum albumin contains no more than 0.1 moles of fatty acids bound to one mole of human serum albumin. In some embodiments, the human serum albumin contains no more than 0.05 moles of fatty acids bound to one mole of human serum albumin. In some embodiments, the human serum albumin contains no more than 0.01 moles of fatty acids bound to one mole of human serum albumin. In some embodiments, the human serum albumin contains no more than 0.001 moles of fatty acids bound to one mole of human serum albumin. In some embodiments, the human serum albumin contains no more than 0.0005 moles of fatty acids bound to one mole of human serum albumin. In some embodiments, the human serum albumin contains no more than 0.0001 moles of fatty acids bound to one mole of human serum albumin.

In some embodiments, the cabozantinib can be a pharmaceutically acceptable salt of cabozantinib. In some embodiments, cabozantinib is a malate salt of cabozantinib. In some embodiments, cabozantinib is a (S)-malate salt of cabozantinib. In some embodiments, cabozantinib can be any one of crystal forms, amorphous forms, solvates and hydrates as described herein.

In some embodiments, the composition is a clear aqueous solution when the composition is dissolved in an aqueous solution. In some embodiments, the aqueous solution is substantially free of solvent other than water. In some embodiments, the aqueous solution is free of solvent other than water.

In some embodiments, the composition is a clear aqueous solution when the composition is dissolved in water. In some embodiments, the composition is a clear aqueous solution when the composition is dissolved in 0.9% saline solution. In some embodiments, the composition is a clear aqueous solution when the composition is dissolved in 5% Dextrose water solution.

In some embodiments, the composition forms a clear aqueous solution, when the composition is dissolved in an aqueous solution, wherein the clear aqueous solution has pH value from about 5 to about 8. In some embodiments, the composition forms a clear aqueous solution, when the composition is dissolved in an aqueous solution, wherein the clear aqueous solution has pH value from about 5.5 to about 7.8. In some embodiments, the composition forms a clear aqueous solution, when the composition is dissolved in an aqueous solution, wherein the clear aqueous solution has pH value from about 6 to about 7.5. In some embodiments, the composition forms a clear aqueous solution, when the composition is dissolved in an aqueous solution, wherein the clear aqueous solution has pH value from about 6.5 to about 7.5. In some embodiments, the composition forms a clear aqueous solution, when the composition is dissolved in an aqueous solution, wherein the clear aqueous solution has pH value from about 6 to about 6.5. In some embodiments, the composition forms a clear aqueous solution, when the composition is dissolved in an aqueous solution, wherein the clear aqueous solution has pH value from about 6.5 to about 7. In some embodiments, the composition forms a clear aqueous solution, when the composition is dissolved in an aqueous solution, wherein the clear aqueous solution has pH value from about 7 to about 7.5. In some embodiments, the composition forms a clear aqueous solution, when the composition is dissolved in an aqueous solution, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous solution is substantially free of solvent other than water. In some embodiments, the aqueous solution is free of solvent other than water.

In some embodiments, the composition forms a clear aqueous solution, when the composition is dissolved in water, wherein the clear aqueous solution has pH value from about 5 to about 8. In some embodiments, the composition forms a clear aqueous solution, when the composition is dissolved in water, wherein the clear aqueous solution has pH value from about 6 to about 7.5. In some embodiments, the composition forms a clear aqueous solution, when the composition is dissolved in water, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

In some embodiments, the composition forms a clear aqueous solution, when the composition is dissolved in 0.9% saline solution, wherein the clear aqueous solution has pH value from about 5 to about 8.

In some embodiments, the composition forms a clear aqueous solution, when the composition is dissolved in 5% Dextrose water solution, wherein the clear aqueous solution has pH value from about 5 to about 8.

In some embodiments, the amount of cabozantinib that is bound to the HSA (e.g., non-covalently) in the aqueous solution (e.g., clear aqueous solution) comprising the composition comprising cabozantinib and HSA (as described herein) is at least 40%, at least 50%, at least 60%, at least 70%, at least 80%, at least 90%, at least 95%, at least 99%, or about 100% of the total about of cabozantinib in the aqueous solution.

In some embodiments, the composition is a clear aqueous solution for at least 1 hour when the composition is dissolved in an aqueous solution. In some embodiments, the composition is a clear aqueous solution for at least 2 hours when the composition is dissolved in an aqueous solution. In some embodiments, the composition is a clear aqueous solution for at least 3 hours when the composition is dissolved in an aqueous solution. In some embodiments, the composition is a clear aqueous solution for at least 4 hours when the composition is dissolved in an aqueous solution. In some embodiments, the composition is a clear aqueous solution for at least 5 hours when the composition is dissolved in an aqueous solution. In some embodiments, the composition is a clear aqueous solution for at least 6 hours when the composition is dissolved in an aqueous solution. In some embodiments, the composition is a clear aqueous solution for at least 8 hours when the composition is dissolved in an aqueous solution. In some embodiments, the composition is a clear aqueous solution for at least 24 hours when the composition is dissolved in an aqueous solution. In some embodiments, the aqueous solution is substantially free of solvent other than water. In some embodiments, the aqueous solution free of solvent other than water.

In some embodiments, the composition is a solid formulation. For example, the solid formulation can be produced in a uniform manner by lyophilization. A skilled artisan would recognize other methods, such as rotary evaporation, that can also produce solid formulations.

In some embodiments, the composition is an aqueous formulation. In some embodiments, the aqueous formulation is substantially free of solvent other than water. In some embodiments, the aqueous formulation is free of solvent other than water.

In some embodiments, the aqueous formulation can be free of a surfactant, such as CREMOPHOR® surfactants and Polysorbate 80. In some embodiments, the aqueous formulation can be substantially free of a surfactant, such as CREMOPHOR® surfactants and Polysorbate 80. In some embodiments, the aqueous formulation can be substantially free of a surfactant selected from the group consisting of CREMOPHOR® surfactants and Polysorbate 80.

In some embodiments, the aqueous formulation is a clear aqueous solution. For example, the formulation can be a clear and stable aqueous solution reconstituted from a sterile lyophilized powder. In some embodiments, the aqueous formulation is a clear aqueous solution, wherein the aqueous formulation is substantially free of solvent other than water. In some embodiments, the aqueous formulation is a clear aqueous solution, wherein the aqueous formulation is free of solvent other than water.

In some embodiments, the aqueous formulation is a clear aqueous solution reconstituted from the solid formulation (e.g. the sterile lyophilized powder) in water. In some embodiments, the aqueous formulation is a clear aqueous solution reconstituted from the solid formulation (e.g. the sterile lyophilized powder) in 0.9% saline solution. In some embodiments, the aqueous formulation is a clear aqueous solution reconstituted from the solid formulation (e.g. the sterile lyophilized powder) in 5% Dextrose water solution.

In some embodiments, the aqueous formulation has pH value from about 5 to about 8. In some embodiments, the aqueous formulation has pH value from about 5.5 to about 7.8. In some embodiments, the aqueous formulation has pH value from about 6 to about 7.5. In some embodiments, the aqueous formulation has pH value from about 6.5 to about 7.5. In some embodiments, the aqueous formulation has pH value from about 6 to about 6.5. In some embodiments, the aqueous formulation has pH value from about 6.5 to about 7. In some embodiments, the aqueous formulation has pH value from about 7 to about 7.5. In some embodiments, the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous formulation is substantially free of solvent other than water. In some embodiments, the aqueous formulation is free of solvent other than water.

In some embodiments, the aqueous formulation is a clear aqueous solution for at least 1 hour. In some embodiments, the aqueous formulation is a clear aqueous solution for at least 1 hour at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 2 hours. In some embodiments, the aqueous formulation is a clear aqueous solution for at least 2 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 3 hours. In some embodiments, the aqueous formulation is a clear aqueous solution for at least 3 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 6 hours. In some embodiments, the aqueous formulation is a clear aqueous solution for at least 6 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 24 hours. In some embodiments, the aqueous formulation is a clear aqueous solution for at least 24 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 3 days. In some embodiments, the aqueous formulation is a clear aqueous solution for at least 3 days when dissolved in an aqueous solution at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least about 1 hour, 2 hours, 3 hours, 4 hours, 5 hours, 6 hours, 8 hours, or 24 hours. In some embodiments, the aqueous formulation is substantially free of solvent other than water. In some embodiments, the aqueous formulation is free of solvent other than water.

In some embodiments, after the aqueous formulation (e.g. a clear aqueous solution) is filtered by a 0.22 micron filter, the amount of cabozantinib in the filtered aqueous solution is at least 96%, 97%, 98%, 99%, or 99.5% of the total amount of cabozantinib in the aqueous solution at the time of dissolution before filtration, wherein the clear aqueous solution has pH value from about 5 to about 8, and wherein the clear aqueous solution is substantially free of solvent other than water. In some embodiments, after the aqueous formulation (e.g. a clear aqueous solution) is filtered by a 0.22 micron filter, the amount of cabozantinib in the filtered aqueous solution is at least 96%, 97%, 98%, 99%, or 99.5% of the total amount of cabozantinib in the aqueous solution at the time of dissolution before filtration, wherein the clear aqueous solution has pH value from about 6 to about 7.5, and wherein the clear aqueous solution is substantially free of solvent other than water. In some embodiments, after the aqueous formulation (e.g. a clear aqueous solution) is filtered by a 0.22 micron filter, the amount of cabozantinib in the filtered aqueous solution is at least 96%, 97%, 98%, 99%, or 99.5% of the total amount of cabozantinib in the aqueous solution at the time of dissolution before filtration, wherein the clear aqueous solution has pH value from about 5 to about 8, and wherein the clear aqueous solution is free of solvent other than water. In some embodiments, after the aqueous formulation (e.g. a clear aqueous solution) is filtered by a 0.22 micron filter, the amount of cabozantinib in the filtered aqueous solution is at least 96%, 97%, 98%, 99%, or 99.5% of the total amount of cabozantinib in the aqueous solution at the time of dissolution before filtration, wherein the clear aqueous solution has pH value from about 6 to about 7.5, and wherein the clear aqueous solution is free of solvent other than water. n some aspects of these embodiments, the aqueous formulation is filtered by a 0.22-micron filter at a time period selected from 1 hour, 2 hours, 3, hours, 4 hours, 5 hours, 6 hours, 12 hours, 18 hours and 24 hours.

Also, provided herein is a pharmaceutical composition comprising the composition consisting essentially of the cabozantinib and the human serum albumin as described herein, and a pharmaceutically acceptable carrier.

In some embodiments, the pharmaceutical composition further comprises at least one anti-cancer drug (e.g., any one of the anti-cancer drugs as described herein).

In some embodiments, the pharmaceutical composition is free of a surfactant, such as CREMOPHOR® surfactants and Polysorbate 80. In some embodiments, the pharmaceutical composition is substantially free of a surfactant, such as CREMOPHOR® surfactants and Polysorbate 80. In some embodiments, the pharmaceutical composition can be substantially free of a surfactant selected from the group consisting of CREMOPHOR® surfactants and Polysorbate 80.

Also, provided herein is a method of treating a proliferative disease comprising the step of administering to a subject in need thereof a pharmaceutical composition comprising the composition consisting essentially of the cabozantinib and the human serum albumin as described herein, and a pharmaceutically acceptable carrier.

Also, provided herein is a method of treating a cancer (e.g., any one of cancers described herein), the method comprising the step of administering to a subject in need thereof of a therapeutically effective amount of a pharmaceutical composition comprising the composition consisting essentially of the cabozantinib and the human serum albumin as described herein, and a pharmaceutically acceptable carrier.

In some embodiments, the cancer is any one of cancers described herein.

In some embodiments, the cancer is a solid tumor. In some embodiments, the cancer is selected from the group consisting of thyroid cancer, renal cell carcinoma (RCC), kidney cancer, hepatocellular cancer, non-small cell lung cancer, ovarian cancer, glioblastoma, melanoma, and colorectal cancer. In some embodiments, the cancer is a thyroid cancer. In some embodiments, the cancer is a metastatic medullary thyroid cancer. In some embodiments, the cancer is a renal cell carcinoma (RCC). In some embodiments, the cancer is an advanced renal cell carcinoma (RCC) who have received prior antiangiogenic therapy. In some embodiments, the cancer is an advanced renal cell carcinoma. In some embodiments the cancer is a kidney cancer. In some embodiments, the cancer is a hepatocellular cancer. In some embodiments, the cancer is a non-small cell lung cancer. In some embodiments, the cancer is a ovarian cancer. In some embodiments, the cancer is a glioblastoma. In some embodiments, the cancer is a melanoma. In some embodiments, the cancer is a colorectal cancer.

In some embodiments, the method of treating cancer (e.g., any one of cancers described herein) comprises the step of administering to a subject in need thereof a therapeutically effective amount of a pharmaceutical composition comprising the composition consisting essentially of the cabozantinib and the human serum albumin as described herein, and a therapeutically effective amount of at least one inhibitor of the kinases for the treatment of cancer described herein.

In some embodiments, the method of treating cancer (e.g. any one of cancers described herein) comprises the step of administering to a subject in need thereof a therapeutically effective amount of a pharmaceutical composition comprising the composition consisting essentially of the cabozantinib and the human serum albumin as described herein, and a therapeutically effective amount of at least one anti-cancer drug described herein.

In some embodiments, a composition consisting essentially of the cabozantinib and the human serum albumin as described herein and an anti-cancer drug are administered simultaneously.

In some embodiments, a composition consisting essentially of the cabozantinib and the human serum albumin as described herein and an anti-cancer drug are administered consecutively.

In some embodiments, the composition is administrated intravenously.

The methods described herein may be performed alone or in conjunction with another therapy, such as surgery, radiation, chemotherapy, immunotherapy, gene therapy, and the like. Additionally, a person having a greater risk of developing the proliferative disease may receive treatments to inhibit or and/or delay the development of the disease.

As will be understood by those of ordinary skill in the art, the appropriate doses of cabozantinib will be approximately those already employed in clinical therapies wherein cabozantinib is administered alone or in combination with other chemotherapeutic agents. Variation in dosage will likely occur depending on the condition being treated. Appropriate effective doses will also vary, as recognized by those skilled in the art, depending on the severity of the disease, the route of administration, the sex, age and general health condition of the subject, excipient usage, the possibility of co-usage with other therapeutic treatments such as use of other agents, and the judgment of the treating physician. For example, guidance for selecting an effective dose can be determined by reference to the prescribing information for cabozantinib.

Also, provided herein is a composition comprising a non-covalently bound complex consisting essentially of cabozantinib and human serum albumin, wherein the cabozantinib and the human serum albumin in the composition are in a ratio by weight from about 1:5 to about 1:2000.

Kits

The present invention also includes pharmaceutical kits useful, for example, in the treatment or prevention of any one of diseases or disorders referred to herein, which include one or more containers containing a pharmaceutical composition comprising a composition of cabozantinib and the human serum albumin as described herein. Such kits can further include, if desired, one or more of various conventional pharmaceutical kit components, such as, for example, containers with one or more pharmaceutically acceptable carriers (e.g., water, saline, or 5% dextrose), additional containers, etc., as will be readily apparent to those skilled in the art. Instructions, either as inserts or as labels, indicating quantities of the components to be administered (e.g., dosage amounts as described herein), guidelines for administration, and/or guidelines for mixing the components, can also be included in the kit.

Methods of Making

Also, provided herein are several methods to prepare a composition comprising a non-covalently bound complex comprising the cabozantinib and the human serum albumin as described herein, a composition comprising the cabozantinib and the human serum albumin as described herein, or a composition consisting essentially of the cabozantinib and the human serum albumin as described herein.

In some embodiments, the present disclosure provides a method of preparing a composition comprising a non-covalently bound complex comprising cabozantinib and human serum albumin, wherein the cabozantinib and the human serum albumin in the composition have a ratio by weight from about 1:5 to about 1:2000.

In some embodiments, the present disclosure provides a method of preparing a composition comprising cabozantinib and human serum albumin, wherein the cabozantinib and the human serum albumin in the composition have a ratio by weight from about 1:5 to about 1:2000.

In some embodiments, the present disclosure provides a method of preparing a composition consisting essentially of cabozantinib and human serum albumin, wherein the cabozantinib and the human serum albumin in the composition have a ratio by weight from about 1:5 to about 1:2000.

In some embodiments, the method comprises mixing an organic solution of cabozantinib in a polar water-miscible organic solvent and a first aqueous solution containing human serum albumin to form a second aqueous solution, wherein the second aqueous solution is a clear aqueous solution.

In some embodiments, the method further comprises removing said polar water-miscible organic solvent and water from the second aqueous solution.

In some embodiments, the method comprises the steps of:
(i) obtaining an organic solution of cabozantinib in a polar water-miscible organic solvent;
(ii) obtaining a first aqueous solution of human serum albumin; and
(iii) mixing the organic solution of cabozantinib and the first aqueous solution of human serum albumin to obtain a second aqueous solution comprising the composition comprising cabozantinib and human serum albumin as described herein.

A non-limiting embodiments of the method are as follows.

Formation of the Organic Solution

In some embodiments, cabozantinib is dissolved in a polar organic solvent (e.g., an alcohol such as methanol, ethanol, isopropanol, and/or n-butanol; THF, $CH_3CN$; DMF; or mixtures thereof) to form an organic solution.

As used herein, the term "organic solution" refers to a solution wherein at least one solvent is a non-aqueous solvent and the weight % of the non-aqueous solvent in the mixture of solvents is at least 50%, at least 60%, at least 70% or at least 90%. In some embodiments, organic solution is a solution in which does not comprise water as a solvent.

In some embodiments, the terms "organic solvent" and "non-aqueous solvent" are used interchangeably and refer to a liquid comprising is at least 50%, at least 60%, at least 70%, at least 90%, or at least 95% of a solvent other than water. In some embodiments, organic solvent is polar (e.g., polar aprotic solvent such as tetrahydrofuran, ethyl acetate, acetone, dimethylformamide, acetonitrile, dimethyl sulfoxide or nitromethane; or a polar protic solvent such as an alcohol, or an acid such as formic acid or an acetic acid). In some embodiments, the organic solvent is water-miscible (i.e., can be mixed with water in all proportions) or water-immiscible (i.e., significant proportions of organic solvent/water do not form a solution).

In some embodiments, the organic solvent is polar organic solvent that is miscible in water (e.g., tetrahydrofuran, propylene glycol, propanol, methanol, ethanol, dimethyl sulfoxide, dimethylformamide, acetonitrile or acetone). In some embodiments, the polar organic solvent is an alcohol. In some embodiments, the polar organic solvent is ethanol or methanol, or mixtures thereof. In some embodiments, the polar organic solvent can be ethanol. In some embodiments, the polar organic solvent is methanol.

In some embodiments, the amount of polar organic solvent (e.g., methanol) is from about 0.005 mL to about 10 mL per 1 mg of cabozantinib. In some embodiments, the amount of polar organic solvent is from about 0.01 mL to about 5 mL per 1 mg of cabozantinib. In some embodiments, the amount of polar organic solvent is from about 0.05 mL to about 5 mL per 1 mg of cabozantinib. In some embodiments, the amount of polar organic solvent is from about 0.1 mL to about 3.0 mL per 1 mg of cabozantinib. In some embodiments, the amount of polar organic solvent is from about 0.2 mL to about 2.0 mL per 1 mg of cabozantinib. In some embodiments, the amount of polar organic solvent is from about 0.5 mL to about 3 mL per 1 mg of cabozantinib. In some embodiments, the amount of polar organic solvent (e.g., methanol) is from about 0.8 mL to about 5.0 mL per 1 mg of cabozantinib. In some embodiments, the amount of polar organic solvent (e.g., methanol) is from about 0.85 mL to about 4.5 mL per 1 mg of cabozantinib. In some embodiments, the amount of polar organic solvent is from about 1 mL to about 3 mL per 1 mg of cabozantinib. In some embodiments, the amount of polar organic solvent is about 0.1 mL, about 0.2 mL, about 0.3 mL, about 0.4 mL, about 0.5 mL, about 0.6 mL, about 0.7 mL, about 0.8 mL, about 0.85 mL, about 0.9 mL, about 1 mL, about 1.3 mL, about 1.4 mL, about 1.5 mL, about 1.6 mL, about 1.7 mL, about 1.8 mL, about 1.9 mL, about 2.0 mL, about 2.1 mL, about 2.6 mL, about 3 mL, about 3.5 mL, about 4.0 mL, about 4.5 mL, or about 5.0 mL per 1 mg of cabozantinib. In some embodiments, the polar organic solvent is methanol and the concentration of cabozantinib in the methanolic solution is from about 0.005 mM to about 10 mM, from about 0.05 mM to about 7 mM, from about 0.1 mM to about 5 mM, or from about 0.5 mM to about 3 mM, from about 0.5 mM to about 2 mM, from about 0.5 mM to about 2.5 mM, or from about 0.6 mM to about 2 mM. In some embodiments, the polar organic solvent is methanol and the concentration of cabozantinib in the methanolic solution is about 0.5 mM, about 0.6 mM, about 0.7 mM, about 0.8 mM, about 0.9 mM, about 1 mM, about 1.1 mM, about 1.2 mM, about 1.3 mM, about 1.4 mM, about 1.5 mM, about 1.6 mM, about 1.7 mM, about 1.9 mM, about 2.0 mM, about 2.1 mM, about 2.2 mM, about 2.3 mM, about 2.4 mM, or about 2.5 mM.

Formation of the First Aqueous Solution

In some embodiments, a defined amount of human serum albumin is dissolved in an amount of water to form a first aqueous solution.

In some embodiments, the amount of aqueous solvent (e.g., water, saline, or a buffer (e.g., any one of buffers described herein)) to prepare the first aqueous solution is from about 1 mL to about 10000 L, from about 2 mL to about 1000 L, from about 3 mL to about 100 L, from about 4 mL to about 10 L, from about 5 mL to about 2 L, from about 6 mL to about 1 L.

In some embodiments, the amount of HSA prepare the first aqueous solution is from about 100 mg to about 1000 kg, from about 150 mg to about 1000 kg, from about 200 mg to about 100 kg, from about 300 mg to about 5 kg, from about 200 mg to about 500 g, or from about 200 mg to about 100 g.

In some embodiments, the amount of aqueous solvent in the first aqueous solution is from about 0.005 mL to about 10 mL per 1 mg of human serum albumin. In some embodiments, the amount of aqueous solvent in the first aqueous solution is from about 0.01 mL to about 5 mL per 1 mg of human serum albumin. In some embodiments, the amount of aqueous solvent in the first aqueous solution is from about 0.01 mL to about 1 mL per 1 mg of human serum albumin. In some embodiments, the amount of aqueous solvent in the first aqueous solution is from about 0.01 mL to about 0.5 mL per 1 mg of human serum albumin. In some embodiments, the amount of aqueous solvent in the first aqueous solution is from about 0.01 mL to about 0.1 mL per 1 mg of human serum albumin. In some embodiments, the amount of aqueous solvent in the first aqueous solution is from about 0.01 mL to about 0.05 mL per 1 mg of human serum albumin. In some embodiments, the amount of aqueous solvent in the first aqueous solution is from about 0.01 mL to about 0.03 mL per 1 mg of human serum albumin. In some embodiments, the amount of aqueous solvent in the first aqueous solution is from about 0.015 mL to about 0.04 mL per 1 mg of human serum albumin. In some embodiments, the amount of aqueous solvent in the first aqueous solution is from about 0.015 mL to about 0.025 mL per 1 mg of human serum albumin. In some embodiments, the amount of aqueous solvent in the first aqueous solution is about 0.007 mL, about 0.01 mL, about 0.015 mL, about 0.02 mL, about 0.025 mL, about 0.03 mL, about 0.035 mL, about 0.04 mL, about 0.045 mL, or about 0.05 mL per 1 mg of human serum albumin. In some embodiments, the amount of aqueous solvent in the first aqueous solution is about 0.02 mL per 1 mg of human serum albumin. In some embodiments, the amount of aqueous solvent (e.g., water) to prepare the first aqueous solution is from about or from about 0.005 mL to about 1 mL, from about 0.015 mL to about 0.5 mL, from about 0.015 mL to about 0.2 mL, from about 0.015 mL to about 0.1 mL, or from about 0.015 mL to about 0.05 mL per 1 mg of HSA. In some embodiments, the amount of aqueous solvent (e.g., water) to prepare the first aqueous solution is about 0.01 mL, about 0.015 mL, about 0.019 mL about 0.02 mL, about 0.021 mL, about 0.022 mL, about 0.023 mL, about 0.024 mL, about 0.025 mL, about 0.026 mL, about 0.027 mL, about 0.028 mL, about 0.029 mL or about 0.03 mL per 1 mg of HSA.

In some embodiments, the preparation of the organic solution and the preparation of the first aqueous solution are performed concurrently.

In some embodiments, the preparation of the organic solution and the preparation of the first aqueous solution are performed sequentially. In some embodiments, the preparation of the organic solution is performed before the preparation of the first aqueous solution. In some embodiments, the preparation of the first aqueous solution is performed before the preparation of the organic solution.

In some embodiments, the range of pH in the first aqueous solution is from about 3 to about 9, from about 4 to about 8, from about 5 to about 7, from about 6 to about 7, from about 3 to about 5, from about 3 to about 7, from about 4 to about 6, or from about 6 to about 6. In some embodiments, the pH of the first aqueous solution is about 4, about 5, about 6, about 6.4, about 6.5, about 6.6, about 6.7, about 6.8, about 6.9, about 7, about 7.1, about 7.2, about 7.3, about 7.4, about 7.5, or about 8.

Formation of the Second Aqueous Solution

In some embodiments, the organic solution of cabozantinib is mixed with the first aqueous solution of human serum albumin to form a second aqueous solution. In some embodiments, the second aqueous solution is a clear aqueous solution.

In some embodiments, the volume ratio of the amount of water to the amount of the polar organic solvent is in a range from about 1:1 to about 1000:1. In some embodiments, the volume ratio of the amount of water to the amount of the polar organic solvent is in a range from about 1.5:1 to about 100:1. In some embodiments, the volume ratio of the amount of water to the amount of the polar organic solvent is in a range from about 1.5:1 to about 20:1. In some embodiments, the volume ratio of the amount of water to the amount of the polar organic solvent is in a range from about 1.5:1 to about 10:1. In some embodiments, the volume ratio of the amount of water to the amount of the polar organic solvent is in a range from about 2:1 to about 10:1. In some embodiments, the volume ratio of the amount of water to the amount of the polar organic solvent is in a range from about 2:1 to about 2.5:1. In some embodiments, the volume ratio of the amount of water to the amount of the polar organic solvent is about 1.5:1, about 2:1, about 2.2:1, about 2.3:1, about 2.4:1, about 2.5:1, about 3:1, about 4:1, about 5:1, about 6:1, about 7:1, about 8:1, about 9:1, or about 10:1.

In some embodiments, the organic solution is added to the first aqueous solution to form a second aqueous solution. In some embodiments, the organic solution is added dropwise to the first aqueous solution to form a second aqueous solution. In some embodiments, the first aqueous solution is added to the organic solution to form a second aqueous solution. In some embodiments, the mixing is performed with agitation. In some embodiments, the mixing is performed with stirring. In some embodiments, the mixing is performed with shaking.

In some embodiments, the addition is done at the temperature from about 0° C. to about 35° C. In some embodiments, the addition is done at the temperature from about 0° C. to about 25° C. In some embodiments, the addition is done at the temperature from about 0° C. to about 10° C. In some embodiments, the addition is done at the temperature from about 0° C. to about 5° C. In some embodiments, the addition is done at the temperature about 0° C. In some embodiments, the addition is done at the temperature about 5° C. In some embodiments, the addition is done at the temperature about 10° C.

In some embodiments, the time of addition is in a range from about 0.1 min to about 24 hours. In some embodiments, the time of addition is in a range from about 1 min to about 2 hour. In some embodiments, the time of addition is in a range from about 1 min to about 1 hour. In some embodiments, the time of addition is in a range from about 5 min to about 30 min.

In some embodiments, the rate of addition of organic solution to the first aqueous solution is from about 0.01 mL/min to about 100 mL/min, from about 0.02 mL/min to about 50 mL/min, from about 0.05 mL/min to about 20 mL/min, from about 1 mL/min to about 10 mL/min, or from about 0.01 mL/min to about 10 mL/min, from about 0.01 mL/min to about 5 mL/min, from about 0.01 mL/min to about 2 mL/min, from about 0.01 mL/min to about 1 mL/min, from about 0.01 mL/min to about 0.5 mL/min, or from about 0.01 mL/min to about 0.1 mL/min.

In some embodiments, the rate of addition of organic solution to the first aqueous solution is about 0.01 mL/min, 0.02 mL/min, 0.03 mL/min, 0.04 mL/min, 0.05 mL/min, 0.1 mL/min, 0.2 mL/min, 0.3 mL/min, 0.5 mL/min, 0.6 mL/min, 0.8 mL/min, 1 mL/min, 1.5 mL/min, 2 mL/min, 3 mL/min, 5 mL/min or 10 mL/min.

In some embodiments, the resulting composition comprising the cabozantinib and the human serum albumin can have any ratio by weight of the cabozantinib to the human serum albumin as described herein. In some embodiments, the human serum albumin is a fatty acid free human serum albumin. In some embodiments, the human serum albumin is essentially fatty acid free.

In some embodiments, the range of pH in the second aqueous solution is from about 3 to about 9, from about 4 to about 8, from about 5 to about 7, from about 6 to about 7, from about 3 to about 5, from about 3 to about 7, from about 4 to about 6, or from about 6 to about 6. In some embodiments, the pH of the second aqueous solution is about 4, about 5, about 6, about 6.4, about 6.5, about 6.6, about 6.7, about 6.8, about 6.9, about 7, about 7.1, about 7.2, about 7.3, about 7.4, about 7.5, or about 8.

Removal of Organic Solvent

In some embodiments, upon completion of mixing of the organic solution with the first aqueous solution to form the second aqueous solution, the polar organic solvent is removed from the second aqueous solution.

In some embodiments, the polar organic solvent is removed under reduced pressure. In some embodiments, the polar organic solvent is removed using rotary evaporation. In some embodiments, the polar organic solvent is removed under a vacuum.

In some embodiments, the removal of the polar organic solvent yields a clear aqueous solution. In some embodiments, water is removed from the aqueous under a vacuum. In some embodiments, water is removed from the aqueous solution using rotary evaporation. In some embodiments, water is removed from the aqueous solution by lyophilization.

In some embodiments, the solvents including both water and organic solvent are removed from the second aqueous solution simultaneously to provide a solid composition. In some embodiments, the solvents are removed under a vacuum. In some embodiments, the solvents are removed using rotary evaporation. In some embodiments, the solvents are removed by lyophilization. In some embodiments, the second aqueous solution was filtered before removal of the solvents.

Removal of Water from the Second Aqueous Solution

In some embodiments, upon removal of the organic solvent from the second aqueous solution, the water can be removed from the second aqueous solution to provide a solid composition.

In some embodiments, the second aqueous solution is filtered before removal of water. For example, the second aqueous solution can be filtered by a 0.22 micron filter before removal of water.

As used herein, the term "micron" refers to a unit of measure of one one-thousandth of a millimeter.

In some embodiments, the water is removed under a vacuum. In some embodiments, the water is removed using rotary evaporation. In some embodiments, the water is removed by lyophilization.

In some embodiments, the amount of cabozantinib that is bound to the HSA (e.g., non-covalently) in the solid composition comprising the composition comprising cabozantinib and HSA (as described herein) is at least 40%, at least 50%, at least 60%, at least 70%, at least 80%, at least 90%, at least 95%, at least 99%, or about 100% of the total about of cabozantinib in the solid composition.

Reconstitution of the Solid

In some embodiments the solid composition comprising the cabozantinib and the human serum albumin (e.g., the solid composition prepared by removing organic solvent from the second aqueous solution and removing water from the second aqueous solution) is mixed with an aqueous solution. In some embodiments, the aqueous solution is a saline solution. In some embodiments, the aqueous solution is a 5% dextrose water solution. In some embodiments, the mixing is the addition of the aqueous solution to the solid. In some embodiments, the mixing is the addition of the solid to the aqueous solution. In some embodiments, the mixing reconstitutes the solid. In some embodiments, the mixing yields a clear aqueous solution. In some embodiments, the pH of the reconstituted solution is from about 3 to about 9, from about 4 to about 8, from about 5 to about 7, from about 6 to about 7, from about 3 to about 5, from about 3 to about 7, from about 4 to about 6, or from about 6 to about 6. In some embodiments, the pH of the reconstituted solution is about 4, about 5, about 6, about 6.4, about 6.5, about 6.6, about 6.7, about 6.8, about 6.9, about 7, about 7.1, about 7.2, about 7.3, about 7.4, about 7.5, or about 8.

Unless otherwise defined, all technical and scientific terms used herein have the same meaning as commonly understood by one of ordinary skill in the art to which this disclosure belongs. Methods and materials are described herein for use in the present disclosure; other suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

Composition Prepared by the Process

In some embodiments, the present disclosure provides a composition comprising cabozantinib and human serum albumin, wherein the cabozantinib and the human serum albumin in the composition have a ratio by weight as described herein (e.g., from about 1:5 to about 1:2000), produced by a method comprising the steps of:

(i) obtaining an organic solution of cabozantinib in a polar water-miscible organic solvent;

(ii) obtaining a first aqueous solution of human serum albumin; and (iii) mixing the organic solution of cabozantinib and the first aqueous solution of human serum albumin to obtain a second aqueous solution comprising the composition comprising cabozantinib and human serum albumin.

In some embodiments, the cabozantinib and the human serum albumin in the composition have a ratio by weight from about 1:100 to about 1:2000, from about 1:130 to about 1:1000, from about 1:130 to about 1:500, from about 1:140 to about 1:500, from about 1:150 to about 1:800, from about 1:150 to about 1:700, from about 1:150 to about 1:600, from about 1:150 to about 1:500, from about 1:150 to about 1:400, from about 1:150 to about 1:350, from about 1:150 to about 1:300, from about 1:160 to about 1:700, from about 1:160 to about 1:600, from about 1:160 to about 1:500, from about 1:160 to about 1:400, from about 1:160 to about 1:350, from about 1:160 to about 1:300, from about 1:165 to about 1:700, from about 1:165 to about 1:600, from about 1:165 to about 1:500, from about 1:165 to about 1:400, from about 1:165 to about 1:350, from about 1:165 to about 1:300, from about 1:170 to about 1:700, from about 1:170 to about 1:600, from about 1:170 to about 1:500, from about 1:170 to about 1:400, from about 1:170 to about 1:350, from about 1:170 to about 1:300, from about 1:150 to about 1:250, from about 1:160 to about 1:250, from about 1:165 to about 1:250, or from about 1:170 to about 1:250. In some embodiments, the cabozantinib and the human serum albumin have a ratio by weight of about 1:130, about 1:140, about 1:150, about 1:155, about 1:160, about 1:162.5, about 165, about 1:170, about 1:175, about 1:180, about 1:190, about 1:200, about 1:210, about 1:220, about 1:230, about 1:240, about 1:250, about 1:260, about 1:270, or about 1:280, about 1:290, about 1:300, about 1:350, about 1:400, or about 1:500.

In some embodiments, the cabozantinib can be a pharmaceutically acceptable salt of cabozantinib. In some embodiments, cabozantinib is a malate salt of cabozantinib. In some embodiments, cabozantinib is a (S)-malate salt of cabozantinib. In some embodiments, cabozantinib can be any one of crystal forms, amorphous forms, solvates and hydrates as described herein.

In some embodiments, the human serum albumin is essentially fatty acid free.

In some embodiments, the composition comprises a non-covalently bound complex comprising cabozantinib and human serum albumin.

In some embodiments, the amount of polar water-miscible organic solvent is from about 0.005 mL to about 10 mL per 1 mg of cabozantinib. In some embodiments, the amount of polar organic solvent is from about 0.01 mL to about 5 mL per 1 mg of cabozantinib. In some embodiments, the amount of polar organic solvent is from about 0.05 mL to about 5 mL per 1 mg of cabozantinib. In some embodiments, the amount of polar organic solvent is from about 0.1 mL to about 3.0 mL per 1 mg of cabozantinib. In some embodiments, the amount of polar organic solvent is from about 0.2 mL to about 2.0 mL per 1 mg of cabozantinib. In some embodiments, the amount of polar organic solvent is from about 0.5 mL to about 3 mL per 1 mg of cabozantinib. In some embodiments, the amount of polar organic solvent is from about 1 mL to about 3 mL per 1 mg of cabozantinib. In some embodiments, the amount of polar organic solvent is about 0.1 mL, about 0.2 mL, about 0.3 mL, about 0.4 mL, about 0.5 mL, about 0.6 mL, about 0.7 mL, about 0.8 mL, about 1 mL, about 1.3 mL, about 1.4 mL, about 1.5 mL, about 1.6 mL, about 1.7 mL, about 1.8 mL, about 1.9 mL, about 2.1 mL, about 2.6 mL, or about 3 mL per 1 mg of cabozantinib. In some embodiments, the polar organic solvent is methanol and the concentration of cabozantinib in the methanolic solution is from about 0.005 mM to about 10 mM, from about 0.05 mM to about 7 mM, from about 0.1 mM to about 5 mM, or from about 0.5 mM to about 3 mM, from about 0.5 mM to about 2 mM, or from about 0.6 mM to about 2 mM. In some embodiments, the polar organic solvent is methanol and the concentration of cabozantinib in the methanolic solution is about 0.6 mM, about 0.7 mM, about 0.8 mM, about 0.9 mM, about 1 mM, about 1.1 mM, about 1.2 mM, about 1.3 mM, about 1.5 mM, about 1.6 mM, about 1.7 mM, or about 1.9 mM.

In some embodiments, the amount of aqueous solvent in the first aqueous solution is from about 0.008 mL to about 0.05 mL per 1 mg of human serum albumin.

In some embodiments, the amount of aqueous solvent in the first aqueous solution is from about 0.01 mL to about 0.04 mL or from about 0.015 mL to about 0.022 mL per 1 mg of human serum albumin.

In some embodiments, the amount of aqueous solvent in the first aqueous solution is from about 0.005 mL to about 10 mL per 1 mg of human serum albumin. In some embodiments, the amount of aqueous solvent in the first aqueous solution is from about 0.01 mL to about 5 mL per 1 mg of human serum albumin. In some embodiments, the amount of aqueous solvent in the first aqueous solution is from about 0.01 mL to about 1 mL per 1 mg of human serum albumin. In some embodiments, the amount of aqueous solvent in the first aqueous solution is from about 0.01 mL to about 0.5 mL per 1 mg of human serum albumin. In some embodiments, the amount of aqueous solvent in the first aqueous solution is from about 0.01 mL to about 0.1 mL per 1 mg of human serum albumin. In some embodiments, the amount of aqueous solvent in the first aqueous solution is from about 0.01 mL to about 0.05 mL per 1 mg of human serum albumin. In some embodiments, the amount of aqueous solvent in the first aqueous solution is from about 0.015 mL to about 0.04 mL per 1 mg of human serum albumin. In some embodiments, the amount of aqueous solvent in the first aqueous solution is about 0.007 mL, about 0.01 mL, about 0.015 mL, about 0.02 mL, about 0.025 mL, about 0.03 mL, about 0.035 mL, about 0.04 mL, about 0.045 mL, or about 0.05 mL per 1 mg of human serum albumin. In some embodiments, the amount of aqueous solvent (e.g., water) to prepare the first aqueous solution is from about or from about 0.005 mL to about 1 mL, from about 0.015 mL to about 0.5 mL, from about 0.015 mL to about 0.2 mL, from about 0.015 mL to about 0.1 mL, or from about 0.015 mL to about 0.05 mL per 1 mg of HSA. In some embodiments, the amount of aqueous solvent (e.g., water) to prepare the first aqueous solution is about 0.01 mL, about 0.015 mL, about 0.019 mL about 0.02 mL, about 0.021 mL, about 0.022 mL, about 0.023 mL, about 0.024 mL, about 0.025 mL, about 0.026 mL, about 0.027 mL, about 0.028 mL, about 0.029 mL or about 0.03 mL per 1 mg of HSA. In some embodiments, the amount of aqueous solvent in the first aqueous solution about 0.02 mL per 1 mg of human serum albumin.

In some embodiments, the polar water-miscible organic solvent is an alcohol selected from the group consisting of methanol, ethanol, isopropanol, n-butanol, and mixtures thereof.

In some embodiments, the polar water-miscible organic solvent is selected from methanol, ethanol, and mixtures thereof.

In some embodiments, the polar water-miscible organic solvent is methanol.

In some embodiments, the aqueous solvent is water.

In some embodiments, the polar water-miscible organic solvent is methanol and the aqueous solvent in the first aqueous solution is water.

In some embodiments, the mixing comprises adding the organic solution to the first aqueous solution. In some embodiments, wherein the mixing comprises adding the first aqueous solution to the organic solution. In some embodiments, the adding is carried out dropwise. In some embodiments, the adding is carried out for a period of time from several minutes to several hours. In some embodiments, the adding is carried out for a period of time from 2 min to 24 hours. In some embodiments, the adding is carried out for a period of time from 2 min minutes to 12 hours, from 2 min to 6 hours, from 3 min to 3 hours, from 2 min to 1 hour, from 2 min to 30 min, or from 2 min to 25 min.

In some embodiments, the rate of addition of organic solution to the first aqueous solution is from about 0.01 mL/min to about 100 mL/min, from about 0.02 mL/min to about 50 mL/min, from about 0.05 mL/min to about 20 mL/min, from about 1 mL/min to about 10 mL/min, or from about 0.01 mL/min to about 10 mL/min, from about 0.01 mL/min to about 5 mL/min, from about 0.01 mL/min to about 2 mL/min, from about 0.01 mL/min to about 1 mL/min, from about 0.01 mL/min to about 0.5 mL/min, or from about 0.01 mL/min to about 0.1 mL/min.

In some embodiments, the rate of addition of organic solution to the first aqueous solution is about 0.01 mL/min, 0.02 mL/min, 0.03 mL/min, 0.04 mL/min, 0.05 mL/min, 0.1 mL/min, 0.2 mL/min, 0.3 mL/min, 0.5 mL/min, 0.6 mL/min, 0.8 mL/min, 1 mL/min, 1.5 mL/min, 2 mL/min, 3 mL/min, 5 mL/min or 10 mL/min.

In some embodiments, the mixing is carried out at a temperature from about 0° C. to about 25° C. In some embodiments, mixing is carried out at ambient temperature (e.g., about 25° C.). In some embodiments, the mixing is carried out at a temperature from about 0° C. to about 5° C. In some embodiments, the mixing is carried out at about 0° C.

In some embodiments, the volume ratio of the amount of aqueous solvent to the amount of the organic solvent in the second aqueous solution is in a range from about 1:1 to about 1000:1. In some embodiments, the volume ratio of the amount of aqueous solvent to the amount of the organic solvent in the second aqueous solution is in a range from about 1.5:1 to about 100:1. In some embodiments, the volume ratio of the amount of aqueous solvent to the amount of the organic solvent in the second aqueous solution is in a range from about 1.5:1 to about 20:1. In some embodiments, the volume ratio of the amount of aqueous solvent to the amount of the organic solvent in the second aqueous solution is in a range from about 1.5:1 to about 10:1. In some embodiments, the volume ratio of the amount of aqueous solvent to the amount of the organic solvent in the second aqueous solution is in a range from about 2:1 to about 10:1. In some embodiments, the volume ratio of the amount of aqueous solvent to the amount of the organic solvent in the second aqueous solution is about 1.5:1, about 2:1, about 2.2:1, about 2.3:1, about 2.4:1, about 2.5:1, about 3:1, about 4:1, about 5:1, about 6:1, about 7:1, about 8:1, about 9:1, or about 10:1. In some embodiments, the aqueous solvent is water. In some embodiments, the aqueous solvent is water and the organic solvent is an alcohol. In some embodiments, the aqueous solvent is water and the organic solvent is methanol.

In some embodiments, the composition is prepared by further comprising the step of removing the polar water-miscible organic solvent from the second aqueous solution to obtain a third aqueous solution comprising the composition comprising cabozantinib and human serum albumin. In some embodiments, the composition is prepared by further comprising the step of removing aqueous solvent from the third aqueous solution to obtain the composition comprising cabozantinib and human serum albumin.

In some embodiments, the composition is prepared by further comprising the step of removing the organic solvent (e.g. methanol) and the aqueous solvent (e.g., water) from the second aqueous solution to obtain the composition comprising cabozantinib and human serum albumin.

In some embodiments, the removing as carried out in vacuum (e.g., using the rotovap). In some embodiments, the removing is carried out by lyophilization.

In some embodiments, the composition forms a clear aqueous solution when the composition is dissolved in an aqueous solvent, and wherein the solubility of the composition in the aqueous solution is at least 10 mg/ml. In some embodiments, the solubility is at least 0.5 mg/ml, at least 1 mg/ml, at least 2 mg/ml, at least 3 mg/ml, at least 5 mg/ml, at least 8 mg/ml, at least 10 mg/ml, at least 12 mg/ml, at least 15 mg/ml or at least 20 mg/ml.

In some embodiments, the composition is a solid formulation

In some embodiments, the composition is an aqueous formulation. In some embodiments, the aqueous formulation is substantially free of solvent other than water. In some embodiments, the aqueous formulation is free of a surfactant. In some embodiments, the surfactant is selected from the group consisting of CREMOPHOR® surfactants and Polysorbate 80.

In some embodiments, the aqueous formulation is a clear aqueous solution. In some embodiments, the aqueous formulation is a clear aqueous solution for at least 1 hour, at least 2 hours, at least 3 hours, at least 4 hours, at least 5 hours, at least 6 hours, at least 8 hours, or at least 24 hours.

In some embodiments, the present disclosure provides a pharmaceutical composition comprising the composition as prepared by a process as described herein, and a pharmaceutically acceptable carrier.

In some embodiments, the present disclosure provides a method of treating a cancer, the method comprising the step of administering to a subject in need thereof a therapeutically effective amount of the pharmaceutical composition as described herein.

In some embodiments, the cancer is a solid tumor. In some embodiments, the cancer is selected from the group consisting of thyroid cancer, renal cell carcinoma (RCC), kidney cancer, hepatocellular cancer, non-small cell lung cancer, ovarian cancer, glioblastoma, melanoma, and colorectal cancer. In some embodiments, the cancer is a thyroid cancer. In some embodiments, the cancer is a metastatic medullary thyroid cancer. In some embodiments, the cancer is a renal cell carcinoma (RCC). In some embodiments, the cancer is an advanced renal cell carcinoma (RCC) who have received prior antiangiogenic therapy. In some embodiments, the cancer is an advanced renal cell carcinoma. In some embodiments the cancer is a kidney cancer. In some embodiments, the cancer is a hepatocellular cancer. In some embodiments, the cancer is a non-small cell lung cancer. In some embodiments, the cancer is a ovarian cancer. In some embodiments, the cancer is a glioblastoma. In some embodiments, the cancer is a melanoma. In some embodiments, the cancer is a colorectal cancer.

EXAMPLES

Materials and Methods

HPLC Analysis:

The HPLC system used herein is a SHIMADZU LC-10AT vp series system, which consists of a SHIMADZU LC-10AT vp pump, a manual injector, a SHIMADZU CTO-10AS vp column oven, a SHIMADZU SPD-10A vp wavelength detector, and a SHIMADZU LC solution workstation. Waters XTERRA RP10 column (4.6 mm×150 mm, 5 µm) is used as an analytical HPLC column. The column oven temperature is 30° C. Mobile phase is composed of methanol and water (70:30, v/v) and pumped at a flow rate of 1 ml/minute. The effluent is detected at a wavelength of 254 nm using a UV detector. The sample injection amount is 20 µl.

Example 1: Composition Comprising Cabozantinib and Human Serum Albumin (HSA)

The Ratio by Weight of Cabozantinib to HSA Prepared was about 1:162.5.

Cabozantinib (2 mg) was dissolved in methanol (3.5 ml) in a vial to give a clear solution. HSA (325 mg) (native fatty acid free human serum albumin purchased from SeraCare Life Sciences, product code: HS-455-80, which contains fatty acids <0.2 mg/gm) as a powder was dissolved in 7 ml of water in a round bottom flask. The methanol solution of cabozantinib was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution.

Example 2: Composition Comprising Cabozantinib and Human Serum Albumin (HSA)

The Ratio by Weight of Cabozantinib to HSA Prepared was about 1:160.

Cabozantinib (2 mg) was dissolved in methanol (3 ml) in a vial to give a clear solution. HSA (320 mg) (native fatty acid free human serum albumin purchased from SeraCare Life Sciences, product code: HS-455-80, which contains fatty acids <0.2 mg/gm) as a powder was dissolved in 7 ml of water in a round bottom flask. The methanol solution of cabozantinib was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution. This aqueous solution stays clear with no precipitation after 1 hour at room temperature. This aqueous solution stays clear with no precipitation after 2 hours at room temperature. This aqueous solution stays clear with no precipitation after 3 hours at room temperature. This aqueous solution stays clear with no precipitation after 4 hours at room temperature. This aqueous solution stays clear with no precipitation after 5 hours at room temperature. This aqueous solution stays clear with no precipitation after 6 hours at room temperature.

Example 3: Composition Comprising Cabozantinib and Human Serum Albumin (HSA)

The Ratio by Weight of Cabozantinib to HSA Prepared was about 1:165.

Cabozantinib (3 mg) was dissolved in methanol (4.3 ml) in a vial to give a clear solution. HSA (495 mg) (native fatty acid free human serum albumin purchased from SeraCare Life Sciences, product code: HS-455-80, which contains fatty acids <0.2 mg/gm) as a powder was dissolved in 10 ml of water in a round bottom flask. The methanol solution of cabozantinib was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution. This aqueous solution stays clear with no precipitation after 1 hour at room temperature. This aqueous solution stays clear with no precipitation after 2 hours at room temperature. This aqueous solution stays clear with no precipitation after 3 hours at room temperature. This aqueous solution stays clear with no precipitation after 4 hours at room temperature. This aqueous solution stays clear with no precipitation after 5 hours at room temperature. This aqueous solution stays clear with no precipitation after 6 hours at room temperature. This aqueous solution stays clear with no precipitation after 24 hours at room temperature.

Example 4: Composition Comprising Cabozantinib and Human Serum Albumin (HSA)

The Ratio by Weight of Cabozantinib to HSA Prepared was about 1:170.

Cabozantinib (3 mg) was dissolved in methanol (4.3 ml) in a vial to give a clear solution. HSA (510 mg) (native fatty acid free human serum albumin purchased from SeraCare Life Sciences, product code: HS-455-80, which contains fatty acids <0.2 mg/gm) as a powder was dissolved in 10 ml of water in a round bottom flask. The methanol solution of cabozantinib was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution. This aqueous solution stays clear with no precipitation after 1 hour at room temperature. This aqueous solution stays clear with no precipitation after 2 hours at room temperature. This aqueous solution stays clear with no precipitation after 3 hours at room temperature. This aqueous solution stays clear with no precipitation after 4 hours at room temperature. This aqueous solution stays clear with no precipitation after 5 hours at room temperature. This aqueous solution stays clear with no precipitation after 6 hours at room temperature. This aqueous solution stays clear with no precipitation after 24 hours at room temperature.

Example 5: Composition Comprising Cabozantinib and Human Serum Albumin (HSA)

The Ratio by Weight of Cabozantinib to HSA Prepared was about 1:175.

Cabozantinib (2 mg) was dissolved in methanol (3 ml) in a vial to give a clear solution. HSA (350 mg) (native fatty acid free human serum albumin purchased from SeraCare Life Sciences, product code: HS-455-80, which contains fatty acids <0.2 mg/gm) as a powder was dissolved in 7 ml of water in a round bottom flask. The methanol solution of cabozantinib was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution. This aqueous solution stays clear with no precipitation after 1 hour at room temperature. This aqueous solution stays clear with no precipitation after 2 hours at room temperature. This aqueous solution stays clear with no precipitation after 3 hours at room temperature. This aqueous solution stays clear with no precipitation after 4 hours at room temperature. This aqueous solution stays clear with no precipitation after 5 hours at room temperature. This aqueous solution stays clear with no precipitation after 6 hours at room temperature. This aqueous solution stays clear with no precipitation after 24 hours at room temperature.

Example 6: Composition Comprising Cabozantinib and Human Serum Albumin (HSA)

The Ratio by Weight of Cabozantinib to HSA Prepared was about 1:170.

Cabozantinib (20 mg) was dissolved in methanol (29 ml) in a vial to give a clear solution. HSA (3400 mg) (native fatty acid free human serum albumin purchased from SeraCare Life Sciences, product code: HS-455-80, which contains fatty acids <0.2 mg/gm) as a powder was dissolved in 68 ml of water in a round bottom flask. The methanol solution of cabozantinib was added slowly dropwise into the flask of the HSA solution with rapid stirring at 0° C. Upon completion of the addition, a clear solution was obtained. Then, the methanol in the solution was removed under vacuum to give a clear solution. The clear aqueous solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution. This aqueous solution stays clear with no precipitation after 1 hour at room temperature. This aqueous solution stays clear with no precipitation after 2 hours at room temperature. This aqueous solution stays clear with no precipitation after 3 hours at room temperature. This aqueous solution stays clear with no precipitation after 4 hours at room temperature. This aqueous solution stays clear with no precipitation after 5 hours at room temperature. This aqueous solution stays clear with no precipitation after 6 hours at room temperature. This aqueous solution stays clear with no precipitation after 24 hours at room temperature.

Example 7: Composition Comprising Cabozantinib and Human Serum Albumin (HSA)

The Ratio by Weight of Cabozantinib to HSA Prepared was about 1:200.

Cabozantinib (2 mg) was dissolved in methanol (3.6 ml) in a vial to give a clear solution. HSA (400 mg) (native fatty acid free human serum albumin purchased from SeraCare Life Sciences, product code: HS-455-80, which contains fatty acids <0.2 mg/gm) as a powder was dissolved in 8 ml of water in a round bottom flask. The methanol solution of cabozantinib was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution. This aqueous solution stays clear with no precipitation after 1 hour at room temperature. This aqueous solution stays clear with no precipitation after 2 hours at room temperature. This aqueous solution stays clear with no precipitation after 3 hours at room temperature. This aqueous solution stays clear with no precipitation after 4 hours at room temperature. This aqueous solution stays clear with no precipitation after 5 hours at room temperature. This aqueous solution stays clear with no precipitation after 6 hours at room temperature. This aqueous solution stays clear with no precipitation after 24 hours at room temperature.

Example 8: Composition Comprising Cabozantinib and Human Serum Albumin (HSA)

The Ratio by Weight of Cabozantinib to HSA Prepared was about 1:150.

Cabozantinib (2 mg) was dissolved in methanol (2.6 ml) in a vial to give a clear solution. HSA (300 mg) (native fatty acid free human serum albumin purchased from SeraCare Life Sciences, product code: HS-455-80, which contains fatty acids <0.2 mg/gm) as a powder was dissolved in 6 ml of water in a round bottom flask. The methanol solution of cabozantinib was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution.

Example 9: Composition Comprising Cabozantinib and Human Serum Albumin (HSA)

The Ratio by Weight of Cabozantinib to HSA Prepared was about 1:300.

Cabozantinib (2 mg) was dissolved in methanol (5.1 ml) in a vial to give a clear solution. HSA (600 mg) (native fatty acid free human serum albumin purchased from SeraCare Life Sciences, product code: HS-455-80, which contains fatty acids <0.2 mg/gm) as a powder was dissolved in 12 ml of water in a round bottom flask. The methanol solution of cabozantinib was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution. This aqueous solution stays clear with no precipitation after 1 hour at room temperature. This aqueous solution stays clear with no precipitation after 2 hours at room temperature. This aqueous solution stays clear with no precipitation after 3 hours at room temperature. This aqueous solution stays clear with no precipitation after 4 hours at room temperature. This aqueous solution stays clear with no precipitation after 5 hours at room temperature. This aqueous solution stays clear with no precipitation after 6 hours at room temperature.

Example 10: Composition Comprising Cabozantinib and Human Serum Albumin (HSA)

The Ratio by Weight of Cabozantinib to HSA Prepared was about 1:400.

Cabozantinib (1 mg) was dissolved in methanol (3.4 ml) in a vial to give a clear solution. HSA (400 mg) (native fatty acid free human serum albumin purchased from SeraCare Life Sciences, product code: HS-455-80, which contains fatty acids <0.2 mg/gm) as a powder was dissolved in 8 ml of water in a round bottom flask. The methanol solution of cabozantinib was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution.

Example 11: Composition Comprising Cabozantinib and Human Serum Albumin (HSA)

The Ratio by Weight of Cabozantinib to HSA Prepared was about 1:500.

Cabozantinib (1 mg) was dissolved in methanol (4.3 ml) in a vial to give a clear solution. HSA (500 mg) (native fatty acid free human serum albumin purchased from SeraCare Life Sciences, product code: HS-455-80, which contains fatty acids <0.2 mg/gm) as a powder was dissolved in 10 ml of water in a round bottom flask. The methanol solution of cabozantinib was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution.

Example 12: Composition Comprising Cabozantinib and Human Serum Albumin (HSA)

The Ratio by Weight of Cabozantinib to HSA Prepared was about 1:170.

cabozantinib (2 mg) was dissolved in methanol (3 ml) in a vial to give a clear solution. HSA (340 mg) (native fatty acid free human serum albumin purchased from Golden West Biologicals, Inc., CAT#: HA1020) as a powder was dissolved in 7 ml of water in a round bottom flask. The methanol solution of cabozantinib was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution. This aqueous solution stays clear with no precipitation after 1 hour at room temperature. This aqueous solution stays clear with no precipitation after 2 hours at room temperature. This aqueous solution stays clear with no precipitation after 3 hours at room temperature. This aqueous solution stays clear with no precipitation after 4 hours at room temperature. This aqueous solution stays clear with no precipitation after 5 hours at room temperature. This aqueous solution stays clear with no precipitation after 6 hours at room temperature.

Example 13: Composition Comprising Cabozantinib and Human Serum Albumin (HSA)

The Ratio by Weight of Cabozantinib to HSA Prepared was about 1:160.

Cabozantinib (20 mg) was dissolved in methanol (18.4 ml) in a vial to give a clear solution. HSA (3200 mg) (native fatty acid free human serum albumin purchased from SeraCare Life Sciences, product code: HS-455-80, which contains fatty acids <0.2 mg/gm) as a powder was dissolved in 43 ml of water in a round bottom flask. The methanol solution of cabozantinib was added slowly dropwise into the flask of the HSA solution with rapid stirring at 0° C. Upon completion of the addition, a clear solution was obtained. Then, the methanol in the solution was removed under vacuum to give a clear solution. The clear aqueous solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution.

Example 14: Measuring pH Value of the Clear Aqueous Solution Comprising Composition Comprising Cabozantinib and Human Serum Albumin (HSA)

500 mg of the lyophilized solid comprising the composition comprising cabozantinib and HSA (the ratio by weight about 1:170) from Example 6 was dissolved in 10 ml of water to give a clear aqueous solution, which was kept at about 25° C. and measured for pH value. The pH value of the clear aqueous solution is 6.73 (3 measurement points: 6.71, 6.73, and 6.74).

Example 15: Composition Comprising Cabozantinib and Human Serum Albumin (HSA)

The Ratio by Weight of Cabozantinib to HSA Prepared was about 1:170.

Cabozantinib (20 mg) was dissolved in methanol (19.8 ml) in a vial to give a clear solution. HSA (3400 mg) (native fatty acid free human serum albumin purchased from SeraCare Life Sciences, product code: HS-455-80, which contains fatty acids <0.2 mg/gm) as a powder was dissolved in 45 ml of water in a round bottom flask. The methanol solution of cabozantinib was added slowly dropwise into the flask of the HSA solution with rapid stirring at 0° C. Upon completion of the addition, a clear solution was obtained. Then, the methanol in the solution was removed under vacuum to give a clear solution. The clear aqueous solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution.

Example 16: Measuring pH Value of the Clear Aqueous Solution Comprising Composition Comprising Cabozantinib and Human Serum Albumin (HSA)

250 mg of the lyophilized solid comprising the composition comprising cabozantinib and HSA (the ratio by weight about 1:170) from Example 15 was dissolved in 10 ml of water to give a clear aqueous solution, which was kept at about 25° C. and measured for pH value. The pH value of the clear aqueous solution is 6.81 (3 measurement points: 6.80, 6.80, and 6.82).

250 mg of the lyophilized solid comprising the composition comprising cabozantinib and HSA (the ratio by weight about 1:170) from Example 15 was dissolved in 10 ml of 0.9% saline solution, which had pH value about 5.41, to give a clear aqueous solution, which was kept at about 25° C. and measured for pH value. The pH value of the clear aqueous solution is 6.78 (3 measurement points: 6.80, 6.78, and 6.77).

250 mg of the lyophilized solid comprising the composition comprising cabozantinib and HSA (the ratio by weight about 1:170) from Example 15 was dissolved in 10 ml of 5% Dextrose water solution, which had pH value about 4.40, to give a clear aqueous solution, which was kept at about 25° C. and measured for pH value. The pH value of the clear aqueous solution is 6.78 (3 measurement points: 6.78, 6.78, and 6.77).

Example 17: Composition Comprising Cabozantinib and Human Serum Albumin (Recombinant Human Serum Albumin)

The Ratio by Weight of Cabozantinib to HSA Prepared was about 1:200.

Cabozantinib (1 mg) was dissolved in methanol (1.7 ml) in a vial to give a clear solution. HSA (200 mg) (fatty acid free recombinant human serum albumin (no fatty acids detected) purchased from Wuhan Healthgen Biotechnology Corp.) as a powder was dissolved in 4 ml of water in a round bottom flask. The methanol solution of cabozantinib was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution. This aqueous solution stays clear with no precipitation after 1 hour at room temperature. This aqueous solution stays clear with no precipitation after 2 hours at room temperature. This aqueous solution stays clear with no precipitation after 3 hours at room temperature. This aqueous solution stays clear with no precipitation after 4 hours at room temperature. This aqueous solution stays clear with no precipitation after 5 hours at room temperature. This aqueous solution stays clear with no precipitation after 6 hours at room temperature.

Example 18: Measuring the Correlation Between HPLC Peak Area and the Cabozantinib Concentration Methanol solutions of cabozantinib in 6 different concentrations, 0.01 mg/ml, 0.025 mg/ml, 0.0375 mg/ml, 0.05 mg/ml, 0.075 mg/ml and 0.1 mg/ml, were prepared. The 6 cabozantinib methanol solutions were analyzed in HPLC. The peak area and concentration of cabozantinib were correlated using linear regression. The linear regression data is shown as below.

$Y$ (peak area)$=-78981+1.13967E8*X$ (concentration), $R=0.99995$, $P<0.0001$.

Example 19: Measuring the Cabozantinib Concentrations in the Aqueous Solutions Before and after the Filtration at 0 Hour, and after the Filtration at 1 Hour, 2 Hours, 3 Hours, 4 Hours, 5 Hours, 6 Hours, and 24 Hours 2.5 g of the lyophilized solid comprising the composition comprising cabozantinib and HSA (the ratio by weight about 1:170) from Example 6 was dissolved in 50 ml of water to give a clear aqueous solution, which was kept at about 25° C. Immediately after the lyophilized solid was dissolved in water, 6 ml of the clear aqueous solution was taken out from the 50 ml solution. Then 1 ml of the solution was taken out from the 6 ml clear aqueous solution to give the solution CAB-0-0h, and the remaining 5 ml of the solution was filtered by the same 0.22 micron aqueous phase filter at 1 ml at a time to give the solutions CAB-1-0h, CAB-2-0h, CAB-3-0h, CAB-4-0h, and CAB-5-0h. To 200 μl of the solutions CAB-0-0h and CAB-5-0h were added 800 μl of acetonitrile separately. The mixtures were vortexed for seconds and then centrifuged at 4,000 g for 5 minutes. The supernatants were removed and collected followed by injection on HPLC. The same procedure was repeated 2 more times for each of solutions CAB-0-0h and CAB-5-0h. Based on the HPLC data and the measurement data of example 16, the cabozantinib concentrations of the solutions of CAB-0-0h, and CAB-5-0h have been calculated and shown in the Table 1. At 0 hour, the cabozantinib concentration of the clear aqueous solution after the filtration was about 99.84% of the cabozantinib concentration of the clear aqueous solution before the filtration.

TABLE 1

| Solution Number | Cabozantinib Concentration (mg/ml) | Average Cabozantinib Concentration (mg/ml) |
|---|---|---|
| CAB-0-0h-1 | 0.2498 | |
| CAB-0-0h-2 | 0.2504 | |
| CAB-0-0h-3 | 0.2496 | |
| CAB-5-0h-1 | 0.2493 | |
| CAB-5-0h-2 | 0.2495 | |
| CAB-5-0h-3 | 0.2498 | |

At 1 hour, 5 ml of the clear aqueous solution was taken out from the remaining 44 ml of the aqueous solution. Then 1 ml of the solution was taken out from the 5 ml clear aqueous solution and filtered by a 0.22 micron aqueous phase filter to give the solution CAB-1-1h, and the remaining 4 ml of the solution was filtered by the same 0.22 micron aqueous phase filter at 1 ml at a time to give the solutions CAB-2-1h, CAB-3-1h, CAB-4-1h, and CAB-5-1h. To 200 μl of the solution CAB-5-1h was added 800 μl of acetonitrile. The mixture was vortexed for seconds and then centrifuged at 4,000 g for 5 minutes. The supernatant was removed and collected followed by injection on HPLC. The same procedure was repeated 2 more times for the solution CAB-5-1h. Based on the HPLC data and the measurement data of example 16, the cabozantinib concentrations of the solution CAB-5-1h have been calculated and shown in the Table 2. At 1 hour, the cabozantinib concentration of the clear aqueous solution after the filtration was about 99.44% of the cabozantinib concentration of the clear aqueous solution at 0 hour before the filtration.

TABLE 2

| Solution Number | Cabozantinib Concentration (mg/ml) | Average Cabozantinib Concentration (mg/ml) |
| --- | --- | --- |
| CAB-5-1h-1 | 0.2488 | |
| CAB-5-1h-2 | 0.2486 | |
| CAB-5-1h-3 | 0.2481 | |

At 2 hours, 5 ml of the clear aqueous solution was taken out from the remaining 39 ml of the aqueous solution. The experiments were done for the 5 ml of the clear aqueous solution taken out at 2 hour using the same protocol as for the 5 ml of the clear aqueous solution taken out at 1 hour. Based on the HPLC data and the measurement data of example 16, the cabozantinib concentrations of the solution CAB-5-2h have been calculated and shown in the Table 3. At 2 hours, the cabozantinib concentration of the clear aqueous solution after the filtration was about 98.76% of the cabozantinib concentration of the clear aqueous solution at 0 hour before the filtration.

TABLE 3

| Solution Number | Cabozantinib Concentration (mg/ml) | Average Cabozantinib Concentration (mg/ml) |
| --- | --- | --- |
| CAB-5-2h-1 | 0.2468 | |
| CAB-5-2h-2 | 0.2469 | |
| CAB-5-2h-3 | 0.2468 | |

At 3 hours, 5 ml of the clear aqueous solution was taken out from the remaining 34 ml of the aqueous solution. The experiments were done for the 5 ml of the clear aqueous solution taken out at 3 hours using the same protocol as for the 5 ml of the clear aqueous solution taken out at 1 hour. Based on the HPLC data and the measurement data of example 16, the cabozantinib concentrations of the solution CAB-5-3h have been calculated and shown in the Table 4. At 3 hours, the cabozantinib concentration of the clear aqueous solution after the filtration was about 98.20% of the cabozantinib concentration of the clear aqueous solution at 0 hour before the filtration.

TABLE 4

| Solution Number | Cabozantinib Concentration (mg/ml) | Average Cabozantinib Concentration (mg/ml) |
| --- | --- | --- |
| CAB-5-3h-1 | 0.2449 | |
| CAB-5-3h-2 | 0.2454 | |
| CAB-5-3h-3 | 0.2458 | |

At 4 hours, 5 ml of the clear aqueous solution was taken out from the remaining 29 ml of the aqueous solution. The experiments were done for the 5 ml of the clear aqueous solution taken out at 4 hour using the same protocol as for the 5 ml of the clear aqueous solution taken out at 1 hour. Based on the HPLC data and the measurement data of example 16, the cabozantinib concentrations of the solution CAB-5-4h have been calculated and shown in the Table 5. At 4 hours, the cabozantinib concentration of the clear aqueous solution after the filtration was about 98.32% of the cabozantinib concentration of the clear aqueous solution at 0 hour before the filtration.

TABLE 5

| Solution Number | Cabozantinib Concentration (mg/ml) | Average Cabozantinib Concentration (mg/ml) |
| --- | --- | --- |
| CAB-5-4h-1 | 0.2455 | |
| CAB-5-4h-2 | 0.2453 | |
| CAB-5-4h-3 | 0.2462 | |

At 5 hours, 5 ml of the clear aqueous solution was taken out from the remaining 24 ml of the aqueous solution. The experiments were done for the 5 ml of the clear aqueous solution taken out at 5 hour using the same protocol as for the 5 ml of the clear aqueous solution taken out at 1 hour. Based on the HPLC data and the measurement data of example 16, the cabozantinib concentrations of the solution CAB-5-5h have been calculated and shown in the Table 6. At 5 hours, the cabozantinib concentration of the clear aqueous solution after the filtration was about 97.64% of the cabozantinib concentration of the clear aqueous solution at 0 hour before the filtration.

TABLE 6

| Solution Number | Cabozantinib Concentration (mg/ml) | Average Cabozantinib Concentration (mg/ml) |
| --- | --- | --- |
| CAB-5-5h-1 | 0.2440 | |
| CAB-5-5h-2 | 0.2440 | |
| CAB-5-5h-3 | 0.2439 | |

At 6 hours, 5 ml of the clear aqueous solution was taken out from the remaining 19 ml of the aqueous solution. The experiments were done for the 5 ml of the clear aqueous solution taken out at 6 hours using the same protocol as for the 5 ml of the clear aqueous solution taken out at 1 hour. Based on the HPLC data and the measurement data of example 16, the cabozantinib concentrations of the solution CAB-5-6h have been calculated and shown in the Table 7. At 6 hours, the cabozantinib concentration of the clear aqueous solution after the filtration was about 97.32% of the cabozantinib concentration of the clear aqueous solution at 0 hour before the filtration.

TABLE 7

| Solution Number | Cabozantinib Concentration (mg/ml) | Average Cabozantinib Concentration (mg/ml) |
| --- | --- | --- |
| CAB-5-6h-1 | 0.2434 | |
| CAB-5-6h-2 | 0.2433 | |
| CAB-5-6h-3 | 0.2428 | |

At 24 hours, 5 ml of the clear aqueous solution was taken out from the remaining 14 ml of the aqueous solution. The experiments were done for the 5 ml of the clear aqueous solution taken out at 24 hour using the same protocol as for the 5 ml of the clear aqueous solution taken out at 1 hour. Based on the HPLC data and the measurement data of example 16, the cabozantinib concentrations of the solution CAB-5-24h have been calculated and shown in the Table 8. At 24 hours, the cabozantinib concentration of the clear aqueous solution after the filtration was about 96.40% of the cabozantinib concentration of the clear aqueous solution at 0 hour before the filtration.

TABLE 8

| Solution Number | Cabozantinib Concentration (mg/ml) | Average Cabozantinib Concentration (mg/ml) |
|---|---|---|
| CAB-5-24h-1 | 0.2408 | |
| CAB-5-24h-2 | 0.2410 | |
| CAB-5-24h-3 | 0.2409 | |

Example 20: Measuring the Cabozantinib Concentrations in the Aqueous Solutions Before and after the Filtration at 0 Hour, and after the Filtration at 1 Hour, 2 Hours, 3 Hours, 4 Hours, 5 Hours, 6 Hours, and 24 Hours 2.5 g of the lyophilized solid comprising the composition comprising cabozantinib and HSA (the ratio by weight about 1:160) from Example 13 was dissolved in 50 ml of water to give a clear aqueous solution, which was kept at about 25° C. Immediately after the lyophilized solid was dissolved in water, 6 ml of the clear aqueous solution was taken out from the 50 ml solution. Then 1 ml of the solution was taken out from the 6 ml clear aqueous solution to give the solution CAB-0-0h, and the remaining 5 ml of the solution was filtered by the same 0.22 micron aqueous phase filter at 1 ml at a time to give the solutions CAB-1-0h, CAB-2-0h, CAB-3-0h, CAB-4-0h, and CAB-5-0h. To 200 μl of the solutions CAB-0-0h and CAB-5-0h were added 800 μl of acetonitrile separately. The mixtures were vortexed for seconds and then centrifuged at 4,000 g for 5 minutes. The supernatants were removed and collected followed by injection on HPLC. The same procedure was repeated 2 more times for each of solutions CAB-0-0h and CAB-5-0h. Based on the HPLC data and the measurement data of example 16, the cabozantinib concentrations of the solutions of CAB-0-0h, and CAB-5-0h have been calculated and shown in the Table 9. At 0 hour, the cabozantinib concentration of the clear aqueous solution after the filtration was about 99.89% of the cabozantinib concentration of the clear aqueous solution before the filtration.

TABLE 9

| Solution Number | Cabozantinib Concentration (mg/ml) | Average Cabozantinib Concentration (mg/ml) |
|---|---|---|
| CAB-0-0h-1 | 0.2728 | |
| CAB-0-0h-2 | 0.2728 | |
| CAB-0-0h-3 | 0.2730 | |
| CAB-5-0h-1 | 0.2725 | |
| CAB-5-0h-2 | 0.2725 | |
| CAB-5-0h-3 | 0.2727 | |

At 1 hour, 5 ml of the clear aqueous solution was taken out from the remaining 44 ml of the aqueous solution. Then 1 ml of the solution was taken out from the 5 ml clear aqueous solution and filtered by a 0.22 micron aqueous phase filter to give the solution CAB-1-1h, and the remaining 4 ml of the solution was filtered by the same 0.22 micron aqueous phase filter at 1 ml at a time to give the solutions CAB-2-1h, CAB-3-1h, CAB-4-1h, and CAB-5-1h. To 200 μl of the solution CAB-5-1h was added 800 μl of acetonitrile. The mixture was vortexed for seconds and then centrifuged at 4,000 g for 5 minutes. The supernatant was removed and collected followed by injection on HPLC. The same procedure was repeated 2 more times for the solution CAB-5-1h. Based on the HPLC data and the measurement data of example 16, the cabozantinib concentrations of the solution CAB-5-1h have been calculated and shown in the Table 10. At 1 hour, the cabozantinib concentration of the clear aqueous solution after the filtration was about 99.85% of the cabozantinib concentration of the clear aqueous solution at 0 hour before the filtration.

TABLE 10

| Solution Number | Cabozantinib Concentration (mg/ml) | Average Cabozantinib Concentration (mg/ml) |
|---|---|---|
| CAB-5-1h-1 | 0.2723 | |
| CAB-5-1h-2 | 0.2724 | |
| CAB-5-1h-3 | 0.2727 | |

At 2 hours, 5 ml of the clear aqueous solution was taken out from the remaining 39 ml of the aqueous solution. The experiments were done for the 5 ml of the clear aqueous solution taken out at 2 hour using the same protocol as for the 5 ml of the clear aqueous solution taken out at 1 hour. Based on the HPLC data and the measurement data of example 16, the cabozantinib concentrations of the solution CAB-5-2h have been calculated and shown in the Table 11. At 2 hours, the cabozantinib concentration of the clear aqueous solution after the filtration was about 99.63% of the cabozantinib concentration of the clear aqueous solution at 0 hour before the filtration.

TABLE 11

| Solution Number | Cabozantinib Concentration (mg/ml) | Average Cabozantinib Concentration (mg/ml) |
|---|---|---|
| CAB-5-2h-1 | 0.2718 | |
| CAB-5-2h-2 | 0.2718 | |
| CAB-5-2h-3 | 0.2720 | |

At 3 hours, 5 ml of the clear aqueous solution was taken out from the remaining 34 ml of the aqueous solution. The experiments were done for the 5 ml of the clear aqueous solution taken out at 3 hours using the same protocol as for the 5 ml of the clear aqueous solution taken out at 1 hour. Based on the HPLC data and the measurement data of example 16, the cabozantinib concentrations of the solution CAB-5-3h have been calculated and shown in the Table 12. At 3 hours, the cabozantinib concentration of the clear aqueous solution after the filtration was about 99.38% of the cabozantinib concentration of the clear aqueous solution at 0 hour before the filtration.

TABLE 12

| Solution Number | Cabozantinib Concentration (mg/ml) | Average Cabozantinib Concentration (mg/ml) |
|---|---|---|
| CAB-5-3h-1 | 0.2712 | |
| CAB-5-3h-2 | 0.2712 | |
| CAB-5-3h-3 | 0.2713 | |

At 4 hours, 5 ml of the clear aqueous solution was taken out from the remaining 29 ml of the aqueous solution. The experiments were done for the 5 ml of the clear aqueous solution taken out at 4 hours using the same protocol as for the 5 ml of the clear aqueous solution taken out at 1 hour.

Based on the HPLC data and the measurement data of example 16, the cabozantinib concentrations of the solution CAB-5-4h have been calculated and shown in the Table 13. At 4 hours, the cabozantinib concentration of the clear aqueous solution after the filtration was about 99.12% of the cabozantinib concentration of the clear aqueous solution at 0 hour before the filtration.

TABLE 13

| Solution Number | Cabozantinib Concentration (mg/ml) | Average Cabozantinib Concentration (mg/ml) |
|---|---|---|
| CAB-5-4h-1 | 0.2705 | 0.2705 |
| CAB-5-4h-2 | 0.2705 | |
| CAB-5-4h-3 | 0.2706 | |

At 5 hours, 5 ml of the clear aqueous solution was taken out from the remaining 24 ml of the aqueous solution. The experiments were done for the 5 ml of the clear aqueous solution taken out at 5 hours using the same protocol as for the 5 ml of the clear aqueous solution taken out at 1 hour. Based on the HPLC data and the measurement data of example 16, the cabozantinib concentrations of the solution CAB-5-5h have been calculated and shown in the Table 14. At 5 hours, the cabozantinib concentration of the clear aqueous solution after the filtration was about 98.94% of the cabozantinib concentration of the clear aqueous solution at 0 hour before the filtration.

TABLE 14

| Solution Number | Cabozantinib Concentration (mg/ml) | Average Cabozantinib Concentration (mg/ml) |
|---|---|---|
| CAB-5-5h-1 | 0.2702 | |
| CAB-5-5h-2 | 0.2699 | |
| CAB-5-5h-3 | 0.2698 | |

At 6 hours, 5 ml of the clear aqueous solution was taken out from the remaining 19 ml of the aqueous solution. The experiments were done for the 5 ml of the clear aqueous solution taken out at 6 hours using the same protocol as for the 5 ml of the clear aqueous solution taken out at 1 hour. Based on the HPLC data and the measurement data of example 16, the cabozantinib concentrations of the solution CAB-5-6h have been calculated and shown in the Table 15. At 6 hours, the cabozantinib concentration of the clear aqueous solution after the filtration was about 98.72% of the cabozantinib concentration of the clear aqueous solution at 0 hour before the filtration.

TABLE 15

| Solution Number | Cabozantinib Concentration (mg/ml) | Average Cabozantinib Concentration (mg/ml) |
|---|---|---|
| CAB-5-6h-1 | 0.2692 | |
| CAB-5-6h-2 | 0.2694 | |
| CAB-5-6h-3 | 0.2695 | |

At 24 hours, 5 ml of the clear aqueous solution was taken out from the remaining 14 ml of the aqueous solution. The experiments were done for the 5 ml of the clear aqueous solution taken out at 24 hours using the same protocol as for the 5 ml of the clear aqueous solution taken out at 1 hour. Based on the HPLC data and the measurement data of example 16, the cabozantinib concentrations of the solution CAB-5-24h have been calculated and shown in the Table 16. At 24 hours, the cabozantinib concentration of the clear aqueous solution after the filtration was about 96.74% of the cabozantinib concentration of the clear aqueous solution at 0 hour before the filtration.

TABLE 16

| Solution Number | Cabozantinib Concentration (mg/ml) | Average Cabozantinib Concentration (mg/ml) |
|---|---|---|
| CAB-5-24h-1 | 0.2644 | |
| CAB-5-24h-2 | 0.2638 | |
| CAB-5-24h-3 | 0.2637 | |

Example 21: Composition Comprising Cabozantinib and Human Serum Albumin (HSA)

The Ratio by Weight of Cabozantinib to HSA Prepared was about 1:200.

Cabozantinib (1 mg) was dissolved in methanol (1.7 ml) in a vial to give a clear solution. A solution of HSA (200 mg, 1 ml) (20% human serum albumin solution for infusion (product name: AlbuRx) from CSL Behring) was added into 3 ml of water to give a HSA solution (4 ml) in a round bottom flask. The methanol solution of cabozantinib was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a cloudy solution.

Example 22: Composition Comprising Cabozantinib and Human Serum Albumin (HSA)

The Ratio by Weight of Cabozantinib to HSA Prepared was about 1:250.

Cabozantinib (1 mg) was dissolved in methanol (2.1 ml) in a vial to give a clear solution. A solution of HSA (250 mg, 1.25 ml) (20% human serum albumin solution for infusion (product name: AlbuRx) from CSL Behring) was added into 3.8 ml of water to give a HSA solution (5.05 ml) in a round bottom flask. The methanol solution of cabozantinib was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a cloudy solution.

Example 23: Composition Comprising Cabozantinib and Human Serum Albumin (HSA)

The Ratio by Weight of Cabozantinib to HSA Prepared was about 1:300.

Cabozantinib (1 mg) was dissolved in methanol (2.6 ml) in a vial to give a clear solution. A solution of HSA (300 mg, 1.5 ml) (20% human serum albumin solution for infusion (product name: AlbuRx) from CSL Behring) was added into 4.5 ml of water to give a HSA solution (6 ml) in a round bottom flask. The methanol solution of cabozantinib was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution.

Example 24: Composition Comprising Cabozantinib and Human Serum Albumin (HSA)

The Ratio by Weight of Cabozantinib to HSA Prepared was about 1:130.

Cabozantinib (2 mg) was dissolved in methanol (1.7 ml) in a vial to give a clear solution. HSA (260 mg) (native fatty acid free human serum albumin purchased from SeraCare Life Sciences, product code: HS-455-80, which contains fatty acids <0.2 mg/gm) as a powder was dissolved in 4 ml of water in a round bottom flask. The methanol solution of cabozantinib was added slowly dropwise into the flask of the HSA solution with rapid stirring at 0° C. Upon completion of the addition, a clear solution was obtained. Then, the methanol in the solution was removed under vacuum to give a slightly cloudy solution. The resulting aqueous solution was lyophilized overnight to give a white solid.

A sample of 100 mg of the lyophilized solid was reconstituted by adding 2 mL water to give a cloudy solution.

Example 25: Composition Comprising Cabozantinib and Human Serum Albumin (HSA)

The Ratio by Weight of Cabozantinib to HSA Prepared was about 1:140.

Cabozantinib (2 mg) was dissolved in methanol (1.7 ml) in a vial to give a clear solution. HSA (280 mg) (native fatty acid free human serum albumin purchased from SeraCare Life Sciences, product code: HS-455-80, which contains fatty acids <0.2 mg/gm) as a powder was dissolved in 4 ml of water in a round bottom flask. The methanol solution of cabozantinib was added slowly dropwise into the flask of the HSA solution with rapid stirring at 0° C. Upon completion of the addition, a clear solution was obtained. Then, the methanol in the solution was removed under vacuum to give a slightly cloudy solution. The resulting aqueous solution was lyophilized overnight to give a white solid.

A sample of 100 mg of the lyophilized solid was reconstituted by adding 2 mL water to give a cloudy solution.

Example 26: Composition Comprising Cabozantinib and Human Serum Albumin (HSA)

The Ratio by Weight of Cabozantinib to HSA Prepared was about 1:150.

Cabozantinib (24 mg) was dissolved in methanol (20.6 ml) in a vial to give a clear solution. HSA (3600 mg) (native fatty acid free human serum albumin purchased from SeraCare Life Sciences, product code: HS-455-80, which contains fatty acids <0.2 mg/gm) as a powder was dissolved in 48 ml of water in a round bottom flask. The methanol solution of cabozantinib was added slowly dropwise into the flask of the HSA solution with rapid stirring at 0° C. Upon completion of the addition, a clear solution was obtained. Then, the methanol in the solution was removed under vacuum to give a clear solution. The clear aqueous solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution.

Example 27: Measuring the Absorption of the Composition Comprising the Cabozantinib and HSA by the 0.22 Micron Aqueous Phase Filter in the Filtration 300 mg of the lyophilized powder from the example 13 (the ratio by weight of cabozantinib to HSA is about 1:160) was dissolved in 6 ml of water to form a clear solution. To this clear aqueous solution, 1 ml solution was taken out to give the solution F0; additional 1 ml solution was taken out and filtered by a 0.22 micron aqueous phase filter to give the solution F1; additional 1 ml solution was taken out and filtered through the same 0.22 micron aqueous phase filter used for the solution F1 to give the solution F2; additional 1 ml solution was taken out and filtered through the same 0.22 micron aqueous phase filter used for the solutions F1 and F2 to give the solution F3; additional 1 ml solution was taken out and filtered by the same 0.22 micron aqueous phase filter used for the solutions F1, F2, and F3 to give the solution F4; and additional 1 ml solution was taken out and filtered by the same 0.22 micron aqueous phase filter used for the solutions F1, F2, F3, and F4 to give the solution F5. To 200 µl of the solutions F0, F1, F2, F3, F4, and F5 were added 800 µl of acetonitrile. The mixtures were vortexed for seconds and then centrifuged at 4,000 g for 5 minutes. The supernatants were removed and collected followed by injection on HPLC. Based on the HPLC data, the concentrations of cabozantinib in the solutions of F0, F1, F2, F3, F4, and F5 have been calculated and shown in the Table 17. The concentration of cabozantinib in the solution F1 was significantly lower than the concentration of cabozantinib in the solution of F0, which indicated that the filter membrane absorption was very significant in the beginning. The concentrations of cabozantinib in the follow-up solutions F2, F3, F4, and F5 were increasing, which indicated that the filter membrane absorption became saturated.

TABLE 17

| Solution Number | Cabozantinib Concentration (mg/ml) |
| --- | --- |
| F0 | 0.2688 |
| F1 | 0.2514 |
| F2 | 0.2637 |
| F3 | 0.2658 |
| F4 | 0.2679 |
| F5 | 0.2684 |

Example 28: Measuring the Absorption of the Composition Comprising the Cabozantinib and HSA by the 0.22 Micron Aqueous Phase Filter in the Filtration 300 mg of the lyophilized powder from the example 15 (the ratio by weight of cabozantinib to HSA is about 1:170) was dissolved in 6 ml of water to form a clear solution. To this clear aqueous solution, 1 ml solution was taken out to give the solution F0; additional 1 ml solution was taken out and filtered by a 0.22 micron aqueous phase filter to give the solution F1; additional 1 ml solution was taken out and filtered through the same 0.22 micron aqueous phase filter used for the solution F1 to give the solution F2; additional 1 ml solution was taken out and filtered through the same 0.22 micron aqueous phase filter used for the solutions F1 and F2 to give the solution F3; additional 1 ml solution was taken out and filtered by the same 0.22 micron aqueous phase filter used for the solutions F1, F2, and F3 to give the solution F4; and additional 1 ml solution was taken out and filtered by the same 0.22 micron aqueous phase filter used for the solutions F1, F2, F3, and F4 to give the solution F5. To 200μl of the solutions F0, F1, F2, F3, F4, and F5 were added 800 μl of acetonitrile. The mixtures were vortexed for seconds and then centrifuged at 4,000 g for 5 minutes. The supernatants were removed and collected followed by injection on HPLC. Based on the HPLC data, the concentrations of cabozantinib in the solutions of F0, F1, F2, F3, F4, and F5 have been calculated and shown in the Table 18. The concentration of cabozantinib in the solution F1 was significantly lower than the concentration of cabozantinib in the solution of F0, which indicated that the filter membrane absorption was very significant in the beginning. The concentrations of cabozantinib in the follow-up solutions F2, F3, F4, and F5 were increasing, which indicated that the filter membrane absorption became saturated.

TABLE 18

| Solution Number | Cabozantinib Concentration (mg/ml) |
|---|---|
| F0 | 0.2551 |
| F1 | 0.2411 |
| F2 | 0.2463 |
| F3 | 0.2523 |
| F4 | 0.2539 |
| F5 | 0.2547 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising a non-covalently bound complex comprising cabozantinib and human serum albumin, wherein the cabozantinib and the human serum albumin in the composition have a ratio by weight from about 1:100 to about 1:2000, and wherein the composition is a clear aqueous solution when the composition is dissolved in an aqueous solution.

2. The composition of claim 1, wherein the cabozantinib and the human serum albumin in the composition have a ratio by weight from about 1:150 to about 1:300.

3. A composition comprising cabozantinib and human serum albumin, wherein the cabozantinib and the human serum albumin in the composition have a ratio by weight from about 1:100 to about 1:2000, and wherein the composition is a clear aqueous solution when the composition is dissolved in an aqueous solution.

4. The composition of claim 3, wherein the cabozantinib and the human serum albumin in the composition have a ratio by weight from about 1:130 to about 1:500.

5. The composition of claim 3, wherein the composition is a solid formulation.

6. The composition of claim 3, wherein the composition is an aqueous formulation.

7. The composition of claim 3, wherein the composition is a clear aqueous solution for at least 2 hours, when the composition is dissolved in an aqueous solution.

8. The composition of claim 3, wherein the composition has pH value from about 5 to about 8.

9. The composition of claim 6, wherein after the aqueous formulation is filtered by a 0.22 micron filter, the amount of cabozantinib in the filtered aqueous solution is at least 96% of the total amount of cabozantinib in the aqueous solution before the filtration.

10. The composition of claim 6, wherein after the aqueous formulation is filtered by a 0.22 micron filter, the amount of cabozantinib in the filtered aqueous solution is at least 97% of the total amount of cabozantinib in the aqueous solution before the filtration.

11. The composition of claim 3, produced by a method comprising the steps of:
    (i) obtaining an organic solution of cabozantinib in a polar water-miscible organic solvent;
    (ii) obtaining a first aqueous solution of human serum albumin; and
    (iii) mixing the organic solution of cabozantinib and the first aqueous solution of human serum albumin to obtain a second aqueous solution comprising the composition comprising cabozantinib and human serum albumin.

12. The composition of claim 11, wherein the composition comprises a non-covalently bound complex comprising cabozantinib and human serum albumin.

13. The composition of claim 11, wherein the polar water-miscible organic solvent is ethanol.

14. The composition of claim 11, wherein the composition is prepared by further comprising removing the organic solvent and the aqueous solvent from the second aqueous solution to obtain the composition comprising cabozantinib and human serum albumin, and the removing is carried out by lyophilization.

15. The composition of claim 11, wherein the composition forms a clear aqueous solution when the composition is dissolved in an aqueous solvent, and wherein the solubility of the composition in the aqueous solution is at least 10 mg/ml.

16. The composition of claim 11, wherein the amount of aqueous solvent in the first aqueous solution is from about 0.008 mL to about 0.05 mL per 1 mg of human serum albumin.

* * * * *